US011154215B2

(12) United States Patent
Lee et al.

(10) Patent No.: US 11,154,215 B2
(45) Date of Patent: Oct. 26, 2021

(54) SYSTEM AND METHODS FOR RESPIRATORY MEASUREMENTS USING BREATHING GAS SAMPLES

(71) Applicants: Medipines Corporation, Newport Beach, CA (US); The Regents of the University of California, Oakland, CA (US)

(72) Inventors: Steve Lee, Newport Beach, CA (US); John B. West, La Jolla, CA (US)

(73) Assignee: Medipines Corporation, Yorba Linda, CA (US)

(*) Notice: Subject to any disclaimer, the term of this patent is extended or adjusted under 35 U.S.C. 154(b) by 341 days.

(21) Appl. No.: 15/814,902

(22) Filed: Nov. 16, 2017

(65) Prior Publication Data

US 2018/0153440 A1 Jun. 7, 2018

Related U.S. Application Data

(60) Provisional application No. 62/430,293, filed on Dec. 5, 2016.

(51) Int. Cl.
*A61B 5/085* (2006.01)
*A61B 5/083* (2006.01)
(Continued)

(52) U.S. Cl.
CPC ............ *A61B 5/0833* (2013.01); *A61B 5/083* (2013.01); *A61B 5/0836* (2013.01);
(Continued)

(58) Field of Classification Search
CPC ..... A61B 5/0833; A61B 5/083; A61B 5/0836; A61B 5/14551; A61B 5/097;
(Continued)

(56) References Cited

U.S. PATENT DOCUMENTS 4,869,254 A 9/1989 Stone
5,842,981 A 12/1998 Larsen
(Continued)

FOREIGN PATENT DOCUMENTS

WO 2012/077065 6/2012

OTHER PUBLICATIONS

Proulx J. "Respiratory monitoring: arterial blood gas analysis, pulse oximetry, and end-tidal carbon dioxide analysis." *Clinical Techniques Small Animal Pract.* 1999. vol. 14. pp. 227-230.
(Continued)

*Primary Examiner* — Navin Natnithithadha

(57) ABSTRACT

There is provided a method that includes receiving pulse-oximetry measurements ($SpO_2$) of a patient's peripheral arterial blood oxygen saturation during a first time period, and receiving breathing samples of the patient. The method further includes determining, using breathing samples of the patient, oxygen partial pressure measurements ($P_A O_2$) and carbon dioxide partial pressure measurements ($P_A CO_2$) from exhaled air of the patient during a steady-state breathing of the patient during the first time period. The method also includes determining an arterial oxygen partial pressure ($P_a CO_2$), an oxygen deficit ($P_A O_2 - P_a O_2$) and a respiratory exchange ratio (RQ) of the patient using the pulse-oximetry measurements ($SpO_2$), the oxygen partial pressure measurements ($P_A O_2$) and the carbon dioxide partial pressure measurements ($P_A CO_2$), and generating one or more signals based on the determining of the arterial oxygen partial pressure ($P_a O_2$), the oxygen deficit ($P_A O_2 - P_a O_2$) and the respiratory exchange ratio (RQ) of the patient.

19 Claims, 20 Drawing Sheets

(51) Int. Cl.
*A61B 5/097* (2006.01)
*A61M 16/08* (2006.01)
*A61M 16/00* (2006.01)
*A61B 5/1455* (2006.01)

(52) U.S. Cl.
CPC ..... *A61B 5/14551* (2013.01); *A61M 16/0066* (2013.01); *A61M 16/085* (2014.02); *A61B 5/097* (2013.01); *A61M 16/024* (2017.08); *A61M 2205/3334* (2013.01); *A61M 2230/432* (2013.01)

(58) Field of Classification Search
CPC ............ A61M 16/085; A61M 16/0066; A61M 16/024; A61M 2205/3334; A61M 2230/432
USPC .......................................... 600/529, 532, 538
See application file for complete search history.

(56) References Cited

U.S. PATENT DOCUMENTS

| | | | |
|---|---|---|---|
| 5,978,691 A | 11/1999 | Mills | |
| 6,042,550 A * | 3/2000 | Haryadi | A61B 5/0836 600/481 |
| 6,059,732 A * | 5/2000 | Orr | A61B 5/083 600/531 |
| 6,200,271 B1 * | 3/2001 | Kuck | A61B 5/029 128/204.12 |
| 6,210,342 B1 * | 4/2001 | Kuck | A61B 5/0836 128/204.23 |
| 6,217,524 B1 * | 4/2001 | Orr | A61B 5/0836 128/204.12 |
| 6,241,681 B1 | 6/2001 | Haryadi | |
| 6,258,038 B1 * | 7/2001 | Haryadi | A61B 5/0836 600/481 |
| 6,435,183 B1 * | 8/2002 | Farman | A61M 16/024 128/204.25 |
| 6,575,918 B2 | 6/2003 | Kline | |
| 6,616,614 B2 * | 9/2003 | Webber | A61B 5/02055 600/526 |
| 7,051,735 B2 * | 5/2006 | Mechlenburg | A61M 16/024 128/204.21 |
| 7,063,669 B2 | 6/2006 | Brawner | |
| 7,258,670 B2 | 8/2007 | Bardy | |
| 7,448,378 B2 * | 11/2008 | Hirose | B63C 11/02 128/201.27 |
| 7,993,281 B2 | 8/2011 | Stock | |
| 8,042,537 B2 * | 10/2011 | Mechlenburg | A61B 5/4818 128/204.21 |
| 8,255,029 B2 | 8/2012 | Addison | |
| 8,545,415 B2 | 10/2013 | West | |
| 10,695,526 B2 * | 6/2020 | Loser | A61M 16/205 |
| 10,702,166 B1 * | 7/2020 | Freeman | A61B 5/686 |
| 2003/0055353 A1 * | 3/2003 | Webber | A61B 5/028 600/526 |
| 2003/0213489 A1 * | 11/2003 | Mechlenburg | A61M 16/0051 128/204.18 |
| 2003/0227472 A1 | 12/2003 | Westinskow | |
| 2005/0004711 A1 * | 1/2005 | Hirose | B63C 11/32 700/265 |
| 2006/0112959 A1 * | 6/2006 | Mechlenburg | A61M 16/0069 128/204.21 |
| 2007/0123792 A1 | 5/2007 | Kline | |
| 2012/0041279 A1 * | 2/2012 | Freeman | A61B 5/087 600/301 |
| 2013/0331662 A1 | 12/2013 | Stoian | |
| 2013/0345572 A1 | 12/2013 | Karbing | |
| 2014/0180026 A1 | 6/2014 | Melker | |
| 2015/0328417 A1 * | 11/2015 | Loser | A61M 16/024 128/204.23 |
| 2016/0058346 A1 | 3/2016 | Heinonen | |
| 2020/0329977 A1 * | 10/2020 | Freeman | A61B 5/686 |

OTHER PUBLICATIONS

Severinghaus, J.W. "Simple, Accurate Equations for Human Blood O2 Dissociation Computations." *Journal of Applied Physiology*. 1979 46, 599-602.

Collins, et al. "Relating Oxygen Partial Pressure, Saturation and Content: The Haemoglobin-Oxygen Dissociation Curve." *Breathe (Sheff)*. Sep. 2015, vol. 11, No. 3. pp. 194-201.

Bernet-Buettiker, et al. "Evaluation of a New Combined Transcutaneous Measurement of PCO$_2$/Pulse Oximetry Oxygen Saturation Ear Sensor in Newborn Patients." *Pediatrics*. Jan. 2005, vol. 115, No. 1. pp e64-e70.

Chiappini, et al. "Accuracy of Pulse Oximeter in the Measurement of the Oxyhaemoglobin Saturation." *Eur Respir*. 1998. J 11, pp. 716-719.

John B. West, et al. "A new method for noninvasive measurement of pulmonary gas exchange using expired gas," Respiratory Physiology & Neurobiology 247 (2018) 112-115. 4 pages.

* cited by examiner

| SpO$_2$ (%) | P$_a$O$_2$ (mmHg) |
|---|---|
| 95 | 80 |
| 94 | 74 |
| 93 | 70 |
| 92 | 66 |
| 91 | 63 |
| 90 | 60 |
| 89 | 58 |
| 88 | 52 |
| 87 | 50 |
| 86 | 49 |

SYSTEM AND METHODS FOR RESPIRATORY MEASUREMENTS USING BREATHING GAS SAMPLES

RELATED APPLICATION(S)

The present application claims the benefit of and priority to Provisional Patent Application Ser. No. 62/430,293, filed Dec. 5, 2016, and titled "Systems and Methods for Respiratory Measurements Using Breathing Gas Samples," which is hereby incorporated fully by reference into the present application.

BACKGROUND

It is frequently necessary to measure the efficiency of gas exchange of the lung, which is often essential in many patients with a pulmonary disease, or even normal subjects or patients with lung disease, who are living at high altitude. In such instances, it is common to make a measurement at the time of diagnosis, and perform subsequent measurements in order to follow the progress of the disease. The traditional method of measuring gas exchange is by using arterial blood gases. This typically gives the arterial $PO_2$ (oxygen partial pressure), $PCO_2$ (carbon dioxide partial pressure), and pH (acid base balance of blood). However, such a measurement has some disadvantages, such as being invasive, uncomfortable for the patient, requiring a technically skilled person, having occasional complications, and being expensive. Therefore, it would be valuable to have a non-invasive method of measuring gas exchange efficiency or inefficiency, which is well tolerated by the patient and can be easily repeated.

SUMMARY

There are provided systems and methods for respiratory measurements using breathing gas samples, substantially as shown in and/or described in connection with at least one of the figures, and as set forth more completely in the claims.

DETAILED DESCRIPTION

Figure 1A:
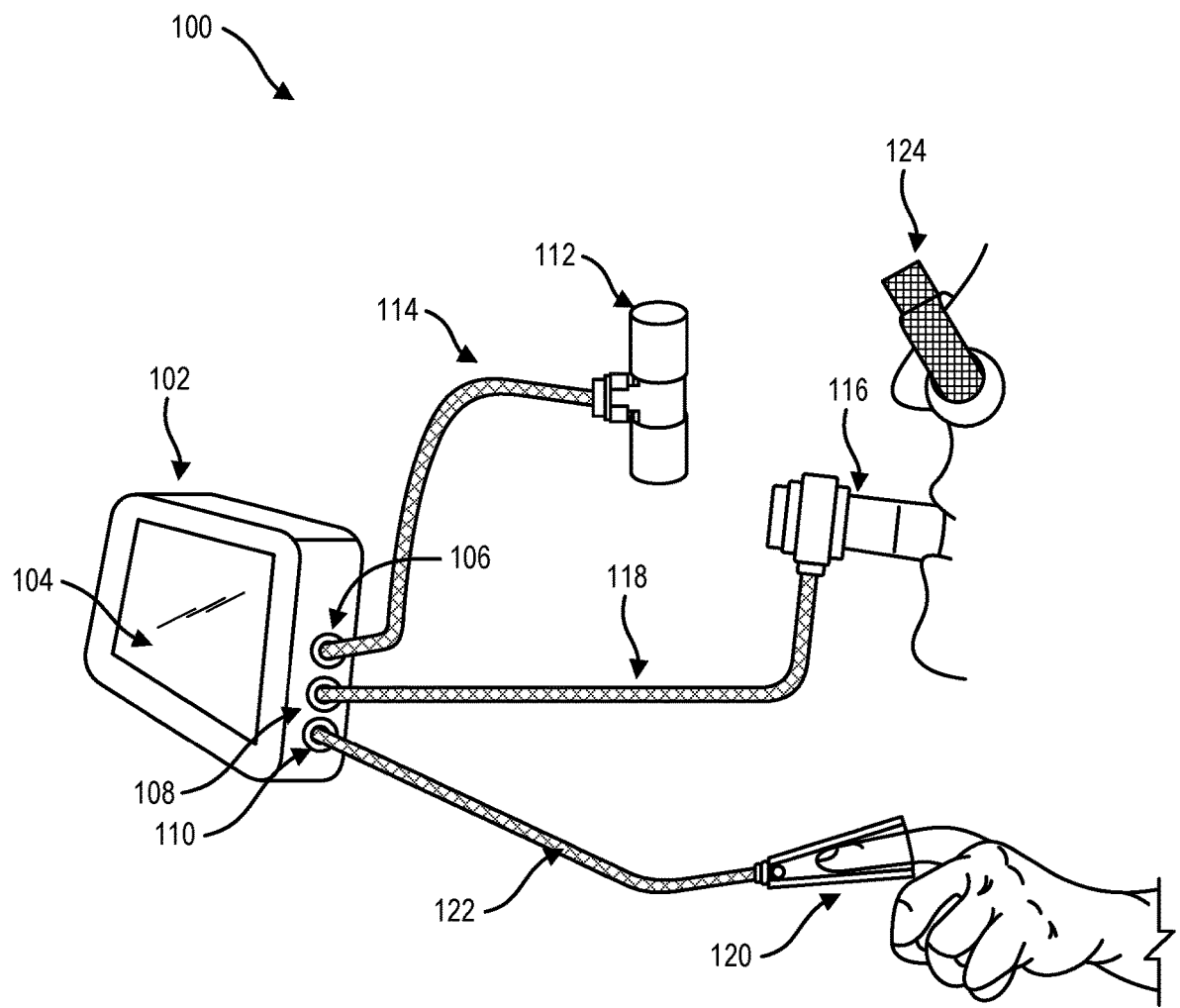
FIG. 1A is a schematic diagram illustrating of an exemplary oximonitor system, according to one implementation of the present disclosure.

The following description contains specific information pertaining to implementations in the present disclosure. One skilled in the art will recognize that the present disclosure may be implemented in a manner different from that specifically discussed herein. The drawings in the present application and their accompanying detailed description are directed to merely exemplary implementations. Unless noted otherwise, like or corresponding elements among the figures may be indicated by like or corresponding reference numerals. Moreover, the drawings and illustrations in the present application are generally not to scale, and are not intended to correspond to actual relative dimensions.

The measurement of oxygen ($O_2$) and carbon dioxide ($CO_2$) levels in the body can provide valuable indications of whether the body is properly receiving and processing oxygen and removing carbon dioxide from the blood. Such measurements can also be indicative of impaired respiratory function, disease, trauma, or other respiratory complications.

Various metrics are generally used in the medical field to measure the effectiveness and efficiency of a patient's breathing and oxygen exchange processes. Physiologically, as a patient breathes, air travels into the patient's lungs and lungs' alveoli or air sacs deep within the lungs, where oxygen is taken up by blood, and carbon dioxide is removed from the blood. Oxygenated blood leaving the lungs is then delivered throughout the patient's body where the oxygen is used by mitochondria within cells.

As used herein, the term "patient" may refer to any human user of an oximonitor system, whether or not such a person is under medical care while using the system. Additionally, in cases where an oximonitor is configured for veterinary use, the term "patient" may include non-human mammals using the system.

The difference between the amount of oxygen available in the alveoli and the amount detected in arterial blood may be indicative of the body's ability to effectively extract, transport, and use oxygen. Traditionally, this is measured by withdrawing arterial blood and testing the blood samples using an arterial blood gas test, typically referred to as an arterial blood gas test (ABG).

The need to draw and test blood samples substantially limits the frequency with which such tests may be performed. However, more frequent monitoring of respiratory status dramatically benefits those with chronic respiratory diseases, such as chronic obstructive pulmonary diseases (COPD), which may include asthma, bronchitis, emphysema, etc. Such diseases may be quickly exacerbated by otherwise relatively minor developments, such as a cold or flu. In such cases, by the time worsening symptoms are apparent, the condition may have dangerously deteriorated.

The ability to quantify arterial oxygen non-invasively (i.e., without penetrating the skin) would open up substantial opportunities to diagnose and monitor breathing related conditions. Additionally, the ability to monitor a wide range of breathing metrics and to regularly transmit data reporting collected metrics to a remote server will enable physicians to identify small changes in long-term trends, allowing for substantial new opportunities to diagnose breathing disorders or to detect worsening breathing conditions before they progress to dangerous levels.

Some implementations of the present disclosure provide systems and methods for non-invasively quantifying arterial oxygen content. In some implementations, systems and methods are provided for contemporaneously measuring two or more breathing-related metrics and using the measured values to estimate an arterial quantity of oxygen based on known relationships modified by certain simplifying assumptions.

The present disclosure uses various abbreviations to refer to measured and calculated quantities. For example, the abbreviation $P_AO_2$ is used to refer to a partial pressure of alveolar oxygen in the patient's lungs, the abbreviation $P_ACO_2$ is used to refer to a partial pressure of alveolar carbon dioxide in the patient's lungs, the abbreviation $P_aO_2$ is used to refer to a partial pressure of arterial oxygen in the patient's blood, and the abbreviation $P_aCO_2$ is used to refer to a partial pressure of arterial carbon dioxide in the patient's blood. In some cases, the abbreviation $PO_2$ may be used to refer to an oxygen partial pressure value where any further distinctions about the nature of the value is assumed to be clear or un-important. Therefore, the abbreviation $PO_2$ may refer to a $P_aO_2$ value, a $P_AO_2$ value, or a different oxygen partial pressure value (e.g., a value based on an arterial blood gas measurement, a measurement of oxygen partial pressure in ambient air, or others).

In some cases, the abbreviation $PCO_2$ as used herein may refer to either $P_ACO_2$ or $P_aCO_2$ based on the assumption that the arterial and alveolar carbon dioxide partial pressure values are frequently sufficiently close to one another that a single measurement of either one may represent both. The abbreviation $SpO_2$ is used to refer to a peripheral oxygen saturation, typically measured in percent by a pulse oximeter. These and other common abbreviations may be used interchangeably with more complete descriptions or names for the same values.

The partial pressure of oxygen in arterial blood, $P_aO_2$, or sometimes referred to as "oxygen tension," is a measurement of the oxygen content in arterial blood (expressed in mmHg). When dealing with gases dissolved in liquids like oxygen in the blood, partial pressure is the pressure that the dissolved gas would have if the blood were allowed to equilibrate with a volume of gas in a container. $P_aO_2$ is very different than $SpO_2$ ("$O_2$ sat" or "oxygen saturation" expressed in %), which measures the ratio of oxygen bound to hemoglobin in red blood cells (RBC). Depending on conditions, hemoglobin releases some percentage of the oxygen molecules to the tissues when the red blood cells pass through the capillaries. We can measure how many of these binding sites are saturated with oxygen. Normal patients have 95-100% oxygen saturation, and when oxygen saturation is below 90%, the patient is deemed "hypoxic." In the past, oxygen saturation was measured through a blood test, but today frequently clinicians use a pulse oximeter to monitor oxygen saturation due to its convenient, non-invasive nature. Oxygen saturation is still a proxy of person's oxygenation status and cannot replace the measure of actual oxygen content in the blood provided by $P_aO_2$ from an arterial blood gas test (ABG). An ABG test involves puncturing an artery with a thin needle and syringe and drawing a small volume of blood from the patient. The most common puncture site is the radial artery at the wrist. The blood can also be drawn from an arterial catheter. An ABG test measures the blood gas tension values of arterial oxygen tension ($P_aO_2$, mmHg), arterial carbon dioxide tension ($P_aCO_2$, mmHg), and arterial oxygen saturation ($S_aO_2$, %) can also be determined. The ABG test is one of the most common tests performed on patients in intensive care units (ICUs) to determine respiratory-blood gas status (e.g., $P_aO_2$, $P_aCO_2$).

The term "A-a gradient" refers to a measure of the difference between the concentration of oxygen in a patient's alveoli (lungs) and the concentration of oxygen in the patient's arterial blood. The A-a gradient is used by clinicians to determine the degree or intensity of hypoxemia (low oxygen level) as well as the source of hypoxemia. For a normal patient, the A-a gradient should be not more than 15 mmHg (depending on the patient's age). A-a gradient values higher than this would be considered elevated in a clinical context. Comparing ABG-derived results for $P_aO_2$ and A-a gradient separately can be vital when caring for patients with critical illness or respiratory disease. Both measures have distinct roles in clinical evaluation. For example, in high altitude settings, the arterial oxygen $P_aO_2$ can be expected to be low but only because the alveolar oxygen ($P_AO_2$) is also low due to a lower partial pressure of oxygen in ambient air with resultant normal A-a gradient and a low $P_aO_2$. However, in states of ventilation-perfusion mismatch, prevalent among COPD patients or pulmonary embolism or right-to-left shunt, oxygen is not effectively transferred from the alveoli to the blood. As a result, a patient may have normal $P_AO_2$ but an elevated A-a gradient.

As used herein, the abbreviation "RQ" may refer to the respiratory exchange ratio, sometimes referred to as the respiratory quotient (RQ). The respiratory quotient measures the ratio of a body's $CO_2$ production to its $O_2$ consumption and is used to assess respiratory state and, in particular, ventilation effectiveness. In equation form: RQ=$CO_2$ produced/$O_2$ consumed. The respiratory quotient is determined by the metabolism of the tissues in a steady-state. Current practice is to use an assumed "normal" RQ value of 0.8 or 0.85 to calculate values such as $P_AO_2$ from ABG test results. For a typical adult, RQ may range from about 0.8 at rest to about 1.0 during exercise. This increase reflects a greater reliance on carbohydrate rather than fat to produce the required energy. Indeed, RQ often reaches even higher levels during the unsteady-state of severe exercise when lactic acid is produced by anaerobic glycolysis, and additional $CO_2$ is therefore eliminated from bicarbonate. RQ is a measure that clinicians use to rapidly assess if a patient's ratio is abnormal (either above 1.0 or below 0.85). Patients with respiratory diseases such as COPD would have higher or lower RQ value at rest than normal healthy adults. This is another indirect measure used as a proxy to assess gas exchange inefficiency at the lung.

Current medical practice is to measure $P_aO_2$ from an arterial blood gas test (ABG) directly, to compute $P_AO_2$ using the alveolar gas equation, and then to compute the A-a gradient from the measured value of $P_aO_2$ and the computed value of $P_AO_2$ from the alveolar gas equation provided below. The equation may be used to calculate $P_AO_2$ using values from ABG or Capnography (to get $PCO_2$ values):

$$P_AO_2 = P_IO_2 - \frac{P_ACO_2}{RQ} + \left[P_ACO_2 * F_IO_2 * \left(\frac{1-RQ}{RQ}\right)\right] \quad \text{(Equation 1)}$$

where $P_IO_2$ is inspired oxygen level, RQ is the respiratory exchange ratio, $F_IO_2$ is the fraction of oxygen in inspired air, and $P_ACO_2$ is the partial pressure of alveolar carbon dioxide from a capnography breath sample or from the results of an ABG test ($P_aCO_2$).

In calculating $P_AO_2$ with the alveolar gas equation, most clinicians use an expected value of RQ as 0.85, which is typically a good approximation but may not be accurate as it does not reflect individual physiology and can lead to an inaccurate value for $P_AO_2$. In some implementations of an oximonitor system, an RQ value may be measured directly from breath samples, taking into account expired $CO_2$ and inspired $O_2$ values (as will be further described below).

Figure 4A:
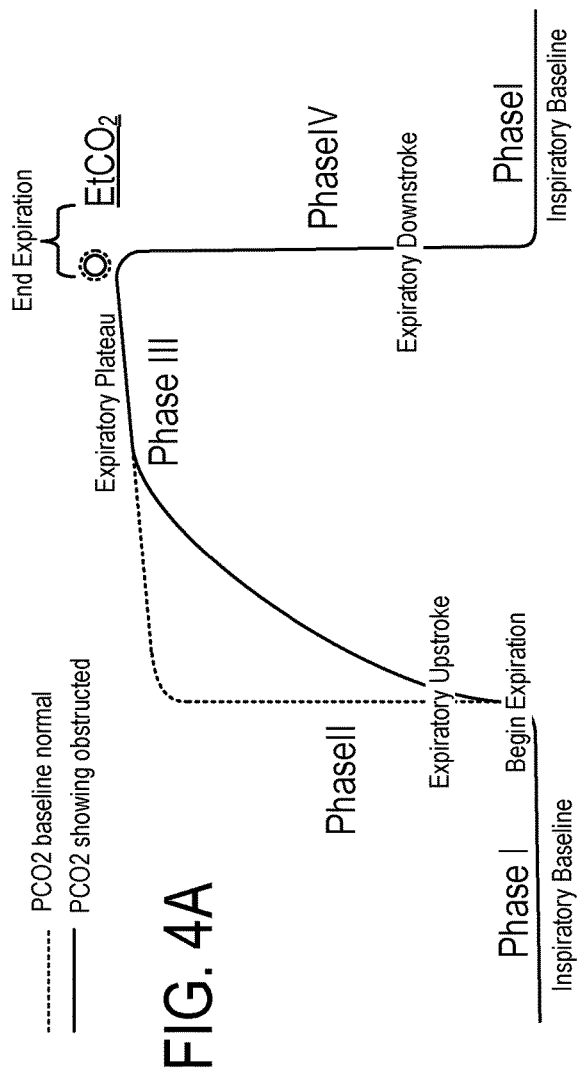
FIG. 4A is a graph diagram illustrating an exemplary waveform representing carbon dioxide measured during a single breath, according to one implementation of the present disclosure.
Figure 4B:
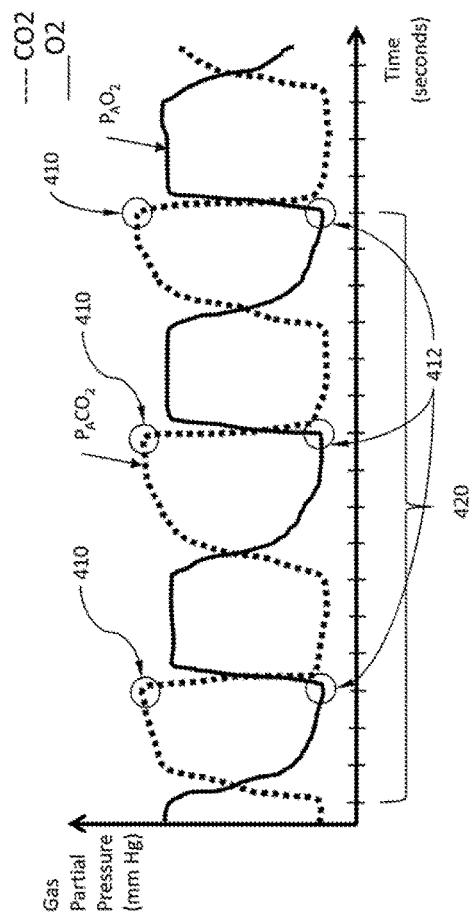
FIG. 4B is a diagram illustrating an exemplary graph of measured alveolar carbon dioxide partial pressure and measured alveolar oxygen partial pressure plotted over time, according to one implementation of the present disclosure.
Figures 4C, 4D:
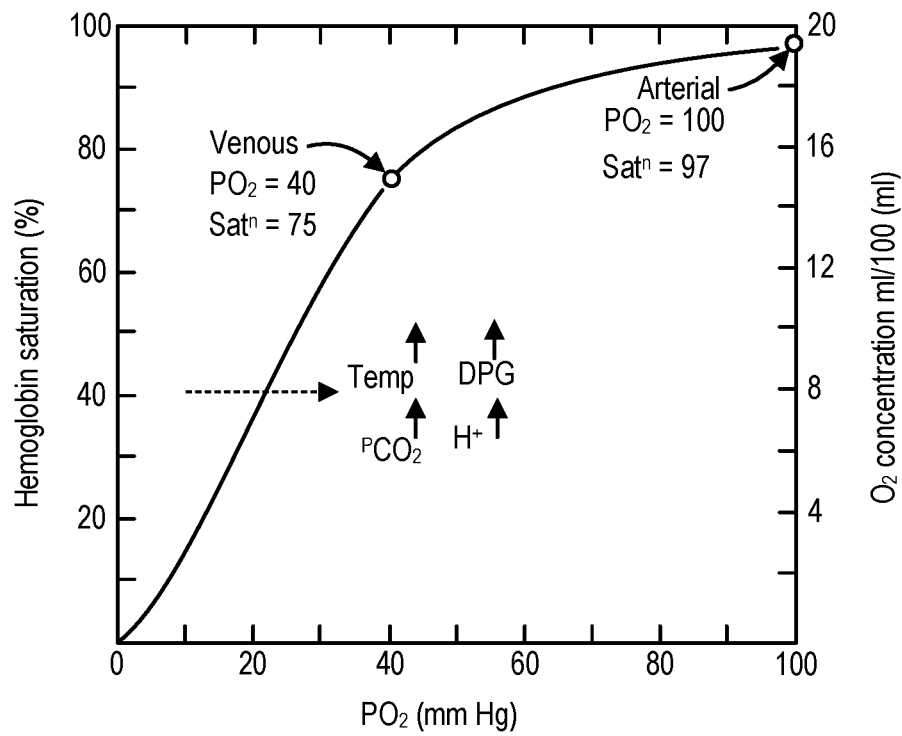
FIG. 4C is a diagram illustrating an exemplary graph of an oxygen dissociation curve and illustrating shifting of the curve depending on changes in various physiologic variables, according to one implementation of the present disclosure.
FIG. 4D is a table illustrating measured oxygen saturation and computed arterial partial pressure at different oxygen saturation values, according to one implementation of the present disclosure.

The relationship between oxygen saturation (%) and oxygen partial pressure (mmHg) follows a well-known medical concept known as the oxygen-hemoglobin dissociation curve with expected normal anchor points at arterial and venous gas levels as shown in FIG. 4C. The normal value for $P_aO_2$ in young adults averages at about 95 mmHg (range from 85 to 100 mmHg). This expected normal value decreases steadily with age. For example, the expected average value is approximately 85 mmHg at age 60 years. One important distinction is that this oxygen-hemoglobin dissociation curve is not standardized across patients but individualized per person depending on individual physiologic changes. For instance, the curve is shifted to right by increase in biochemical compounds such as DPG (2,3-diphosphoglycerate) inside the red blood cells, blood temperature, $PCO_2$ and blood pH.

The various methods and devices described herein may provide for non-invasive measurement of respiratory metrics, including end tidal $O_2$ ($PETO_2$), end tidal $CO_2$ ($PETCO_2$), blood oxygen saturation $SpO_2$, heart rate, and respiratory rate. The various measured values may be used to determine various calculated metrics, including partial pressure of oxygen in arterial blood ($P_aO_2$), a measure substantially equivalent to the Alveolar-arterial gradient (A-a gradient in mmHg) referred to herein as the "oxygen deficit," and a respiratory quotient (RQ) to monitor patient's changing respiratory status. The methods and devices may also allow for pulmonary function tests ($FEV_1$, FVC, $FEV_1$%) with a flow volume loop.

The measured and calculated metrics may be displayed as graphical and/or numerical data for clinicians to monitor and assess patient respiratory status on a real-time basis. The output may comprise a report, record data, or alarm generation. Alarm management may also comprise various outputs, including an audio alarm, a visual alert, or a print-out to inform the patient, nurse, physician, etc. of detected unstable respiratory variations and any potentially risky physiological condition as related to respiratory distress.

In particular, various implementations provide respiratory monitoring systems and software algorithms that allow for the detection of hypoxemia, hypercarbia, impaired gas exchange, acute respiratory events, asthma, pneumonia, respiratory failure, COPD progression, upper respiratory infection, $O_2$—$CO_2$ imbalance, and similar or related conditions. Various implementations may also provide for comprehensive non-invasive respiratory monitoring to allow clinicians to detect changing respiratory conditions for patients rapidly as intervention is needed to adjust medication, therapy, or other forms of management, with a resultant reduction in the number of unnecessary emergency room visits or prolonged critical care and hospitalizations.

Figure 1B:
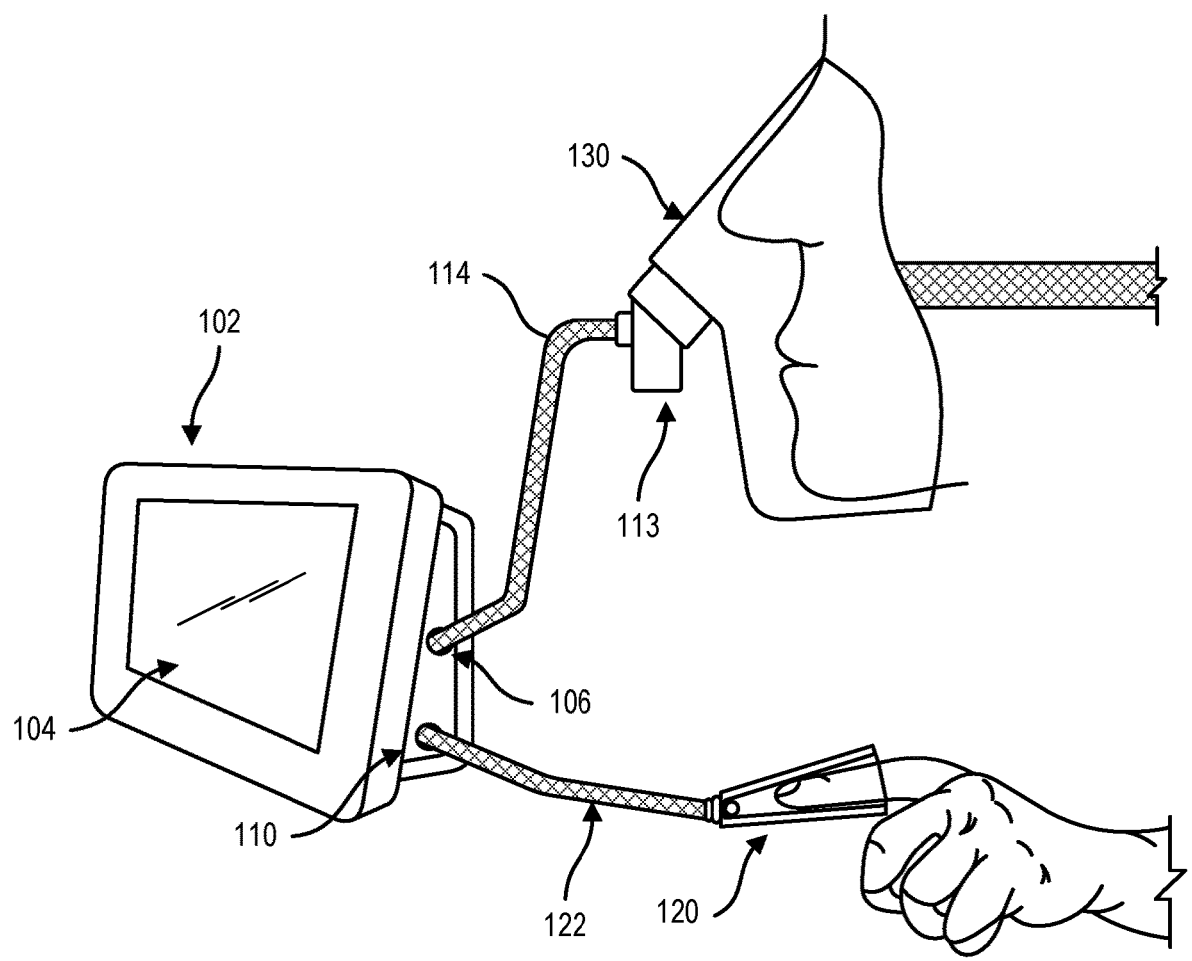
FIG. 1B is a schematic diagram illustrating of an exemplary oximonitor system, according to one implementation of the present disclosure.

FIG. 1A illustrates an example oximonitor system 100, according to one implementation of the present disclosure. Oximonitor system 100 of FIG. 1A, which may be utilized as a medical device, includes control unit 102 which may include display screen 104 and connection ports 106, 108, 110 for receiving various peripheral devices. Peripheral devices may include steady-state breathing tube 112 connectable to port 106 of control unit 102 by transport tube 114, pulmonary mechanics flow tube (PFT) 116 connectable to port 108 of control unit 102 by transport tube and/or cable 118, and pulse oximeter clip device 120 connectable to port 110 of control unit 102 by cable 122 (or wirelessly connected to control unit 102). In some implementations, a patient may wear a nose clip 124 during some tests. In some implementations, a breathing tube 112 may be configured for continuous or un-attended monitoring of a patient's breathing by joining the breathing tube to a device securable to a patient in order to collect samples of exhaled air. For example, a breathing tube 112 may be integrated with or replaced by a face mask 130 as illustrated in FIG. 1B. In some implementations, face masks 130 adapted for use with an oximonitor system may include oxygen masks, face masks designed for use with CPAP (continuous positive airway pressure) or BiPAP (bi-level positive airway pressure) devices, or other related face mask devices.

Face masks 130 may be adapted for use with an oximonitor system by including a substantially resistance-free conduit 113 joining an interior side of the mask to an exterior of the mask and through which the patient may inhale and exhale air while experiencing substantially minimal air-flow resistance relative to breathing without the mask. A transport tube 114 may join the substantially resistance-free conduit 113 to an air-sample intake section of an oximonitor system. In some implementations, a transport tube 114 may be joined directly to the mask.

Similarly, in some implementations, a breathing tube 112 or other resistance-free conduit 113 may be integrated with a nasal cannula which may withdraw samples of breathing air from one or both of a patient's nostrils. In other implementations, a resistance-free conduit 113 and transport tube 114 may be configured to obtain samples of breathing air via a tracheostomy tube, an endotracheal tube, or other conduit through which a patient may breathe. A conduit may be considered "resistance free" if it applies no more than about one PSI.

Figure 2:
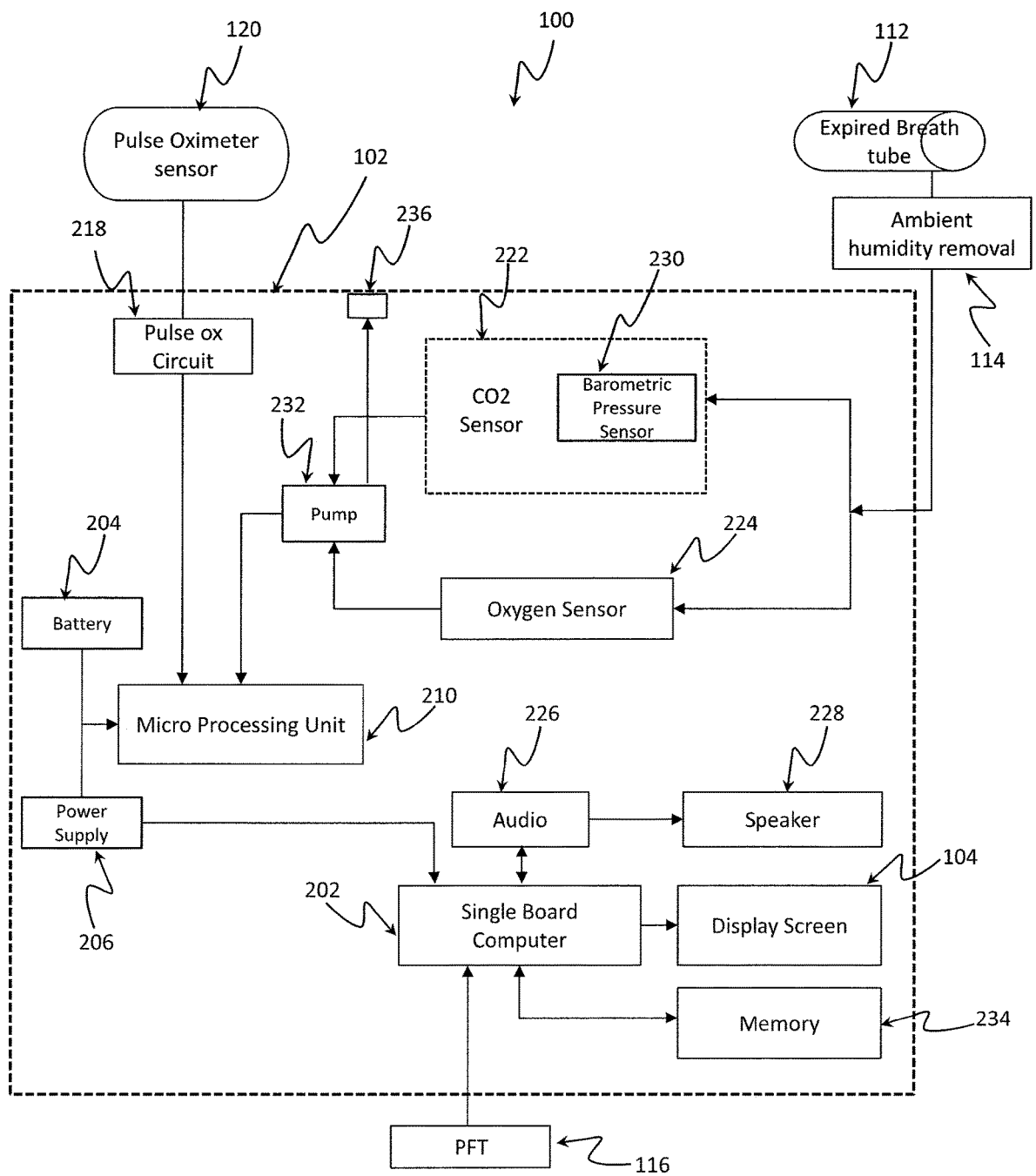
FIG. 2 is a schematic block diagram illustrating exemplary components of an oximonitor system, according to one implementation of the present disclosure.

FIG. 2 is a schematic block diagram illustrating exemplary components of oximonitor system 100, according to one implementation of the present disclosure. Oximonitor system 100 may comprise computing device 202 connected to battery 204 and/or power supply 206. Computing device 202 may be configured to bi-directionally communicate with display screen 104 and with microprocessor or controller 210. Measurement sub-systems may be configured to communicate analog and/or digital signals to controller 210 via the respective connections.

The gas exchange measurement sub-system may include steady-state breathing tube 112 connected to carbon dioxide ($CO_2$) analyzer 222 and oxygen ($O_2$) analyzer 224. Pump 232 may be included to draw gas samples from breathing tube 112, through analyzers 222 and 224, through exit conduits, and out of the system through vent 236. Signal carriers (e.g., wires, fiber optic cables, etc.) may be provided to transmit signals from analyzers 222 and 224 to micro controller 210.

Although a variety of different oxygen sensing devices could be employed in $O_2$ analyzer 224, in one implementation, oxygen analyzer 224 may include an Ultra Fast Oxygen (UFO-130-2) sensor manufactured by Teledyne Analytical Instruments of the City of Industry, Calif. $CO_2$ analyzer 222 may include a CO2WFA carbon dioxide sensor manufactured by Treymed Inc. or a Jaeger HCS $CO_2$ sensor manufactured by VIASYS Healthcare GmbH of Hoechberg, Germany or the Microstream® $CO_2$ sensor manufactured by Oridion Medical Inc. of Needham, Mass. Alternatively, any other gas sensors may be used.

Additionally, other gas analyzers may also be included to measure quantities of additional gases in exhaled and/or inhaled air or ambient air. $O_2$ analyzer 224 and $CO_2$ analyzer 222 may generally be configured to communicate digital or analog signals to controller 210. In various implementations, the analyzers may also include integrated electronics to perform some signal processing or other analysis prior to communicating a signal to controller 210.

With reference to FIG. 1A, in some implementations of the present disclosure, the gas exchange test sub-system may include breathing tube 112 connected to control unit 102 by one or more gas transport tubes 114 configured to transport a gas sample from breathing tube 112 to a port on control unit 102. In some implementations, gas sample transport tube 114 may comprise a drying tube. A suitable drying tube may include as those commercially available from Perma Pure LLC of Toms River, N.J. A drying tube may be included to remove some or all water vapor present in ambient and/or exhaled air samples delivered to the gas analyzers in order to improve the quality of partial pressure measurements reported by the gas analyzers.

With reference to FIG. 1A, FIG. 1B, and FIG. 2, in various implementations, air conduit 113 may comprise any suitable structures such as tubes, pipes, or passages through bulk materials. Pump 232 may comprise any type of pump suitable for transporting the air samples through the gas analyzers 222 and 224. Examples of suitable pump types may include diaphragm pumps, peristaltic pumps, vane pumps, centrifugal pumps, syringe pumps, compressor pumps, and piston pumps. Other pumps for driving air flow through the conduits may also be used. In some implementations, more than one pump may be used.

U.S. Pat. No. 8,545,415 ("the '415 patent"), which is incorporated herein by reference in its entirety, describes systems and methods for measuring alveolar gas levels. Components, devices, and techniques described in the '415 patent may be adapted for use in various implementations of a gas exchange test sub-system as described herein.

The gas exchange measurement sub-system may be configured to measure partial pressure of one or more gases in exhaled air. The partial pressure of a particular gas in a mixed-gas sample represents the hypothetical pressure of that particular gas if it alone occupied the same volume as the mixed-gas sample at the same temperature. Partial pressures are typically measured in units of millimeters of mercury (mm Hg), but may also be presented or used in any other units of pressure, such as atmospheres, bars, pounds per square inch (PSI), pascals (newtons per square meter), torr, etc.

In various implementations, the pulse-oximeter sub-system may include any pulse oximeter device using any available pulse oximetry methods for measuring oxygen saturation. The term "oxygen saturation" refers to the fraction of oxygen-saturated hemoglobin relative to total hemoglobin (unsaturated+saturated) in the blood. Oxygen saturation values are typically reported as percent values, but may also be presented or used as decimal values (i.e., percent value divided by 100).

In the examples illustrated in FIG. 1, FIG. 1B, and FIG. 2, the pulse oximeter sub-system may include finger clip 120 connected to pulse oximetry circuit 218, which may be connected to system controller 210. Pulse oximetry is a non-invasive method for monitoring a person's oxygen saturation. Pulse oximetry readings of $SpO_2$ (peripheral oxygen saturation) may not always be identical to readings of $S_aO_2$ (arterial oxygen saturation) obtained from arterial blood gas analysis, but the two are sufficiently similar that pulse oximetry may be used for measuring oxygen saturation in the various systems and methods described herein.

Pulse oximetry may be performed in a transmissive mode or in a reflective mode. In the transmissive mode, a sensor device may be placed on a thin part of a person's body, such as a fingertip, hand, toe, earlobe, nose, or in the case of an infant, across a foot. A transmissive pulse oximeter may include one or more light transmitters (e.g., lasers, LEDs, or other light sources), which may be configured to pass two different wavelengths of light through the body part to a photodetector located on an opposite side of the body part from the transmitter(s). Digital and/or analog electronics connected to the photodetector may measure the changing absorbance at each of the wavelengths. The electronics may also be configured to determine the absorbance at each of the wavelengths attributable to the pulsing arterial blood alone, excluding venous blood, skin, bone, muscle, fat, nail polish or other structures that may absorb some of the transmitted light.

Reflectance pulse oximetry may be used as an alternative to transmissive pulse oximetery. Reflectance pulse oximetry does not require a thin section of the person's body and is therefore well suited to more universal applications such as the feet, arms, legs, forehead, torso, chest, etc. Instead of evaluating wavelengths of light passing through tissue, reflectance pulse oximeters may receive and evaluate reflected light at desired wavelengths.

In the examples illustrated in FIG. 1A and FIG. 2, the pulmonary mechanics measurement sub-system may generally include flow tube 116 and pulmonary mechanics measurements sub-system may be connected to system controller 210. In some implementations, flow tube 116 may be joined to control unit 102 by a gas transport tube (e.g., if the pulmonary mechanics measurement controller contains pressure sensors or other devices for evaluating pulmonary mechanics). In other implementations, sensors or other devices for evaluating pulmonary mechanics may be integrated into or attached to flow tube 116, in which case flow tube 116 may be connected to control unit 102 by cable 118 configured to carry electrical or optical signals. In some implementations, flow tube 116 may be joined to control unit 102 by both a gas transport tube and a cable. The pulmonary mechanics measurement sub-system may generally include the apparatus and electronics configured to perform a spirometry test.

Spirometry is a pulmonary function test (PFT) that measures the volume and/or speed (flow rate) of air that can be exhaled and/or inhaled. Any of various available types of spirometers, which may use one or more of several different methods for measurement (e.g., pressure transducers, ultrasonic flow measurement, water gauge, mechanical turbines, or other devices), may be used. In some implementations, spirometer components may be selected with a preference for those making the overall device more portable.

In some implementations, a pulmonary mechanics flow tube may be integrated with a steady-state breathing tube, thereby allowing for both functions to be performed using a single breathing tube. In some implementations, a pulmonary mechanics measurement sub-system may be omitted from oximonitor system 100.

In various implementations, display screen 104 may be a touch screen configured to allow a patient or other user to control system 100 and to read output from the system displayed on the screen. System 100 may also include any other user interface devices as desired. For example, system 100 may include any number of buttons, switches, knobs, sliders, dials, levers, or other user interface structures. In some implementations, system 100 may also include an audio output device 226 (e.g., a speaker), an audio input device 228 (e.g., a speaker), and/or an optical input device (e.g., a camera or other optical sensor).

In some implementations, oximonitor system 100 may also include a heart rate monitor, one or more accelerometers, or other measuring devices.

In some implementations, oximonitor system 100 may be configured to perform various tests to collect data and/or information about the state of the patient's breathing, gas exchange, or other aspects of cardiopulmonary health. In some implementations, these tests may include a gas exchange test, a forced expiratory breath test, a symptom survey, and/or other tests.

In various implementations, a test to be performed may be selected using the user interface. In some implementations, once a test has been selected, oximonitor system 100 may display instructions for how the patient should proceed with the test. Alternatively, or in addition, oximonitor system 100 may be configured to detect actions taken by the patient in order to anticipate which test is being performed. For example, if accelerometers or other motion detectors are placed on one or both of the steady-state breathing tube and the flow tube, oximonitor system 100 computing device may detect motion of one of the breathing tubes, and may prepare to receive data for a test associated with that breathing tube. Alternately, oximonitor system 100 may be configured with a standby mode in which it is prepared to accept input from any of the various measurement sub-systems. The oximonitor system may detect a change in a signal received by one or more sensors (such as a change in flow rate through one of the breathing tubes, for example), and may begin storing and collecting data for any tests associated with that sensor.

Figure 3A:
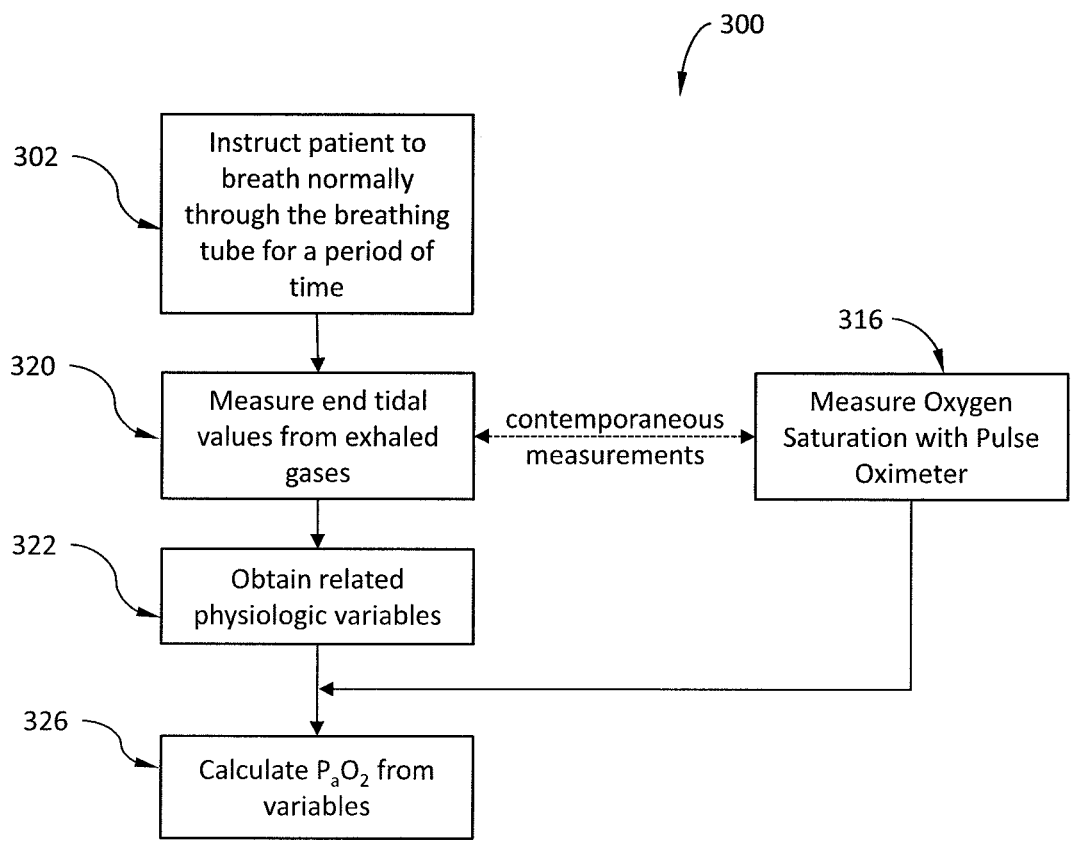
FIG. 3A is a high level process flow diagram illustrating an exemplary process for performing a gas exchange test, according to one implementation of the present disclosure.

In some implementations, oximonitor system 100 may be configured to perform a gas exchange test, which may also be referred to as a steady-state breathing test. FIG. 3A provides a process flow chart illustrating an example of a gas exchange test process 300 that may be performed by the device.

In some implementations, process 300 may begin at block 302 by instructing the patient to breathe normally for a period of time. In some implementations, the gas exchange test may be performed while the patient is breathing at a steady-state; that is, inhaling and exhaling at regular intervals. In some implementations, a metronome may be used to assist a patient to breathe at regular intervals. In other implementations, metronomic functionality may be incorporated into oximonitor system 100.

In some implementations, oximonitor system 100 may instruct the patient to breathe by emitting a first tone indicating that the patient should begin to inhale and then, after a pre-determined period of time, transmitting a second tone (which may be the same as the "inhale" tone or a different tone) indicating that the patient should begin to exhale. By repeatedly alternating between the first tone and the second tone, oximonitor system 100 may direct a patient to breathe steadily for a desired period of time. In some implementations, the step of instructing a patient to breathe normally may be omitted (e.g., if a mask or nasal cannula is in use). In such implementations, the oximonitor system may be configured to identify periods of steady-state breathing.

In some implementations, oximonitor system 100 may monitor $O_2$ and $CO_2$ partial pressure values for consistency over multiple breath cycles (inspiration/expiration cycles). For example, oximonitor system 100 may determine that steady-state breathing is occurring by determining a degree of change in $O_2$ and/or $CO_2$ partial pressure values over a pre-determined number of consecutive breath cycles. If a difference between maximum and minimum $O_2$ and/or $CO_2$ partial pressure values for the evaluated cycles is less than a pre-determined amount, oximonitor system 100 may conclude that breathing is at steady-state during those breathing cycles.

A single breathing cycle (or breath cycle) may be defined as commonly understood in respiratory medicine as a ventilatory cycle consisting of an inspiration followed by the expiration of a volume of gas (which may be called the "tidal volume"). The duration or total cycle time of a breathing cycle may be defined as the breathing or ventilatory period. In some cases, a breathing cycle may be referred to as a respiratory cycle.

In some implementations, oximonitor system 100 may identify a period of steady-state breathing (i.e., based on a time period or a number of breathing cycles) from a much larger data set which may include non-steady-state breathing periods. Oximonitor system 100 then obtains end-tidal values (as described elsewhere herein) from only the breathing cycles in the steady-state breathing period.

In some implementations, a period of steady-state breathing may be determined based on a respiratory exchange ratio (RER) which may be calculated based on a relationship between the oxygen level detected by the oxygen analyzer and the carbon dioxide level detected by the $CO_2$ analyzer. In such implementations, oximonitor system 100 may begin collecting $O_2$ and $CO_2$ partial pressure values immediately upon beginning the gas exchange test, even before determining that the patient is breathing at a steady-state.

In some implementations, a heart rate in combination with respiratory rate may be used for identifying a period of steady-state breathing. For example, a patient's heart rate may be monitored based on a pulse oximetry signal or with a separate heart rate monitoring device such as an electrocardiogram (ECG). A heart rate within a pre-determined range (which may be selected based on the patient, or which may be universally applied) may be indicative of steady-state breathing.

In some implementations, two or more of the above-described methods (or other methods) may be used in combination to detect a steady-state breathing condition.

In some implementations, oximonitor system 100 may be configured to indicate to the patient or other user if a sufficient period of steady-state breathing is or is not achieved during a gas exchange test. For example, in some implementations a green light may be illuminated while the system detects steady-state breathing, and a red light may be illuminated when breathing detected by the system is not at steady-state.

In some implementations, it may be desirable for the patient to breathe at a steady-state for a period of time (e.g., 30 seconds, 1 minute, 1.5 minutes, 2 minutes, etc.) before oximonitor system 100 proceeds to the tests at block 320 and block 316 in the process illustrated in FIG. 3A. In various implementations, gas partial pressure data and oxygen saturation data may be collected even before the patient's breathing reaches steady-state for a period of time. In such implementations, data representing a time period following a desired steady-state breathing time period may be identified and used for the calculations in blocks 322 and 326.

Figure 3B:
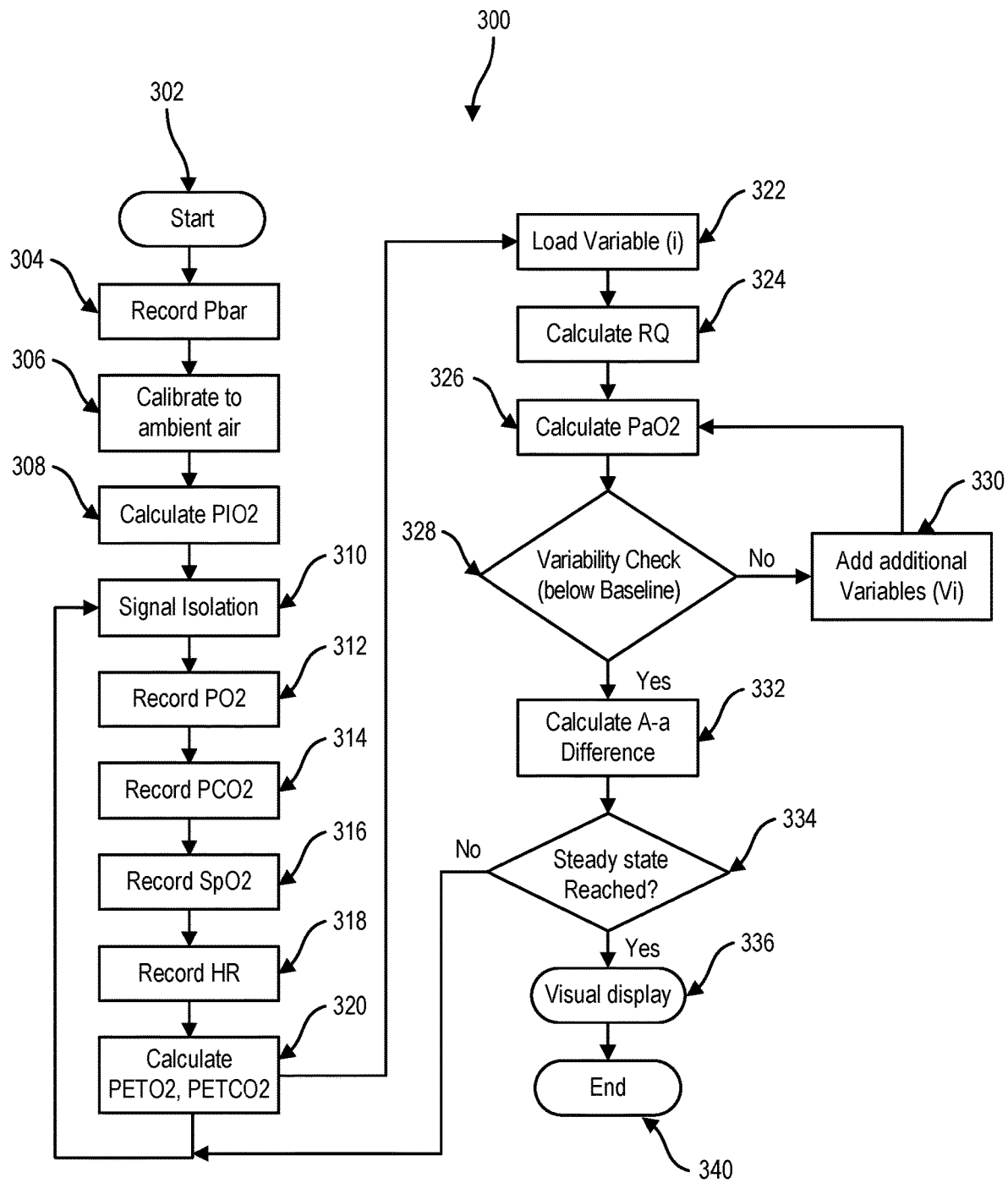
FIG. 3B is a detailed process flow diagram illustrating an exemplary process for performing a gas exchange test, according to one implementation of the present disclosure.

At block 320, oximonitor system 100 may begin calculating the end tidal partial pressures of exhaled gases using the oxygen and carbon dioxide gas analyzers described above. In some implementations, contemporaneously with the gas partial pressure measurements, a blood oxygen saturation ($SpO_2$) measurement may be taken with the pulse oximeter at block 316 for the same time period as the end tidal expired gas measurements 320. In some implementations, a measurement of only one of $P_ACO_2$ and $P_AO_2$ may be contemporaneous with a measurement of $SpO_2$. The environmental gas measurement and gas sampling to computation of arterial $P_aO_2$ and ensuing iterative process used is illustrated in FIG. 3B. The gas exchange measurement sub system starts 302 and the barometric pressure is recorded 304 and the system is calibrated to ambient air 306. $P_IO_2$ is calculated 308 and signal isolation is used to record $PO_2$ 312, $PCO_2$ 314, $SpO_2$ 316 and pulse rate (HR) 318. Once end tidal values are calculated 320, a variable is loaded into the $P_aO_2$ equation 322 and the RQ Value is calculated 324. When the system calculates $P_aO_2$ 326, a variability check using initial computed value against expected value is checked 328, if the value is not within the acceptable range within standard deviation target, then additional variable Vi is added in sequential manner 330 to recalculate $P_aO_2$ 326. After the variability check is confirmed and falls within accepted baseline target 328 then the system calculates the $O_2$ deficit 332 and determines if the system has recorded steady-state breathing pattern 334. If the system has reached steady-state breathing pattern 334, a visual display notifies the user in color green with text notification that steady-state pattern has been reached and session can now be ended 336. User then can end the session by pressing the end button on the screen 340.

As used herein, the term "contemporaneous" in the context of performing two or more measurements refers to events or tests occurring at approximately the same time or during overlapping time periods. Events may be, but need not be simultaneous or concurrent in order to be considered contemporaneous in the present disclosure. For example, a test A and a test B may be described as occurring contemporaneously if instantaneous measurements of test A are taken alternatingly with instantaneous measurements of test B during a common time period. In other words, instantaneous data samples of test A and test B that are collected in an interlaced fashion during an overlapping time period may be described as occurring concurrently. Additionally, instantaneous data samples of test A and test B that are collected simultaneously with one another may be described as occurring concurrently.

A physiological time delay exists between a given breath and a peripheral pulse oximetry measurement representative of blood in the lungs at the time of the given breath. The duration of such a time delay may tend to vary based on a patient's physiology, but is generally on the order of several seconds. In various implementations, measurements of $P_ACO_2$ and/or $P_AO_2$ may be contemporaneous with a measurement of $SpO_2$ if the measurements are taken at the same time as one another (i.e., ignoring any physiological time delay), over a time period at least as long as an expected physiological time delay, or at different times shifted by an approximate physiological time delay (e.g., measurements of $P_ACO_2$ and/or $P_AO_2$ taken at a time "t" may be correlated with $SpO_2$ measurements taken at a time "t+d" where "d" is a physiological time delay).

As used herein, the term "instantaneous" used in reference to a measurement may refer to a single digital data sample or an aggregation or normalization of a group of digital data samples taken from a continuous or intermittent analog signal. As used herein, "collecting" measurements may refer to storing digital data sample values in a non-transitory volatile or non-volatile memory device. Collection of a plurality of instantaneous data samples at regular sampling intervals may be described as "continuous" measurement regardless of the continuousness or intermittency of an analog signal. In some implementations, a "continuous" gas exchange measurement (for example) may persist for multiple breath cycles (inhale/exhale).

Various examples and implementations described herein may refer to a "baseline" value of one or more measurements. Such baseline values may be established in any of a number of ways using an oximonitor system or other suitable devices or methods. For example, in some implementations, a baseline blood gas quantity (e.g., $PCO_2$, $P_aO_2$, or A-a gradient) may be established based on a result of an ABG test. In some implementations, a baseline quantity (e.g., one or more of $P_aCO_2$, $P_aO_2$, $SpO_2$, $P_AO_2$, $P_ACO_2$, oxygen deficit, A-a gradient, pulmonary mechanics quantities, or other quantity) may be an average or "normal" value or range of values based on a population study, a clinical study, or a physician's judgment.

In some implementations, an oximonitor system 100 may be configured to establish a patient-specific baseline quantity (e.g., one or more of $P_aCO_2$, $P_aO_2$, $SpO_2$, $P_AO_2$, $P_ACO_2$, oxygen deficit, A-a gradient, pulmonary mechanics quantities, or other quantity) based on one or more measurements and/or calculations performed by the oximonitor system itself.

As explained elsewhere herein, some implementations of an oximonitor system may determine an "end-tidal value" for $P_ACO_2$ and/or $P_AO_2$ during each inhale/exhale breathing cycle. Based on such measurements, the oximonitor may calculate a value of $P_aO_2$ and $O_2$ deficit for each breathing cycle. Thus, an oximonitor system may establish a baseline value by calculating a mean, median, maximum, or minimum of any measured or calculated value (e.g., $P_AO_2$, $PCO_2$, $P_aO_2$, or $O_2$ deficit) over a pre-determined number of breathing cycles, or over an arbitrary number of breathing cycles that may occur within a pre-determined period of time. In some implementations, an oximonitor system may be configured to allow an operator to designate a period of measurement time (or a number of breathing cycles) over which a baseline value is to be determined. In some implementations, a mean, median, maximum, or minimum value may be continuously updated based on a trailing period of time or number of breathing cycles.

As used herein, the phrase "trailing period" may refer to a defined period of time or a defined integer number of breathing cycles that is continuously updated in a first-in-first-out manner similar to a circular buffer. For example, a trailing period of three breathing cycles may be defined as the three most recently completed breathing cycles. As each new breathing cycle completes, information associated with the first breathing cycle may be dropped and replaced by information associated with the new breathing cycle.

Measurements of $P_IO_2$, $P_AO_2$, $P_ACO_2$ and $SpO_2$ may vary depending on various complex and inter-related factors, such as an amount of recent physical activity of the patient, supplemental oxygen presence, the patient's recent diet, the patient's heart rate and/or breathing rate, the patient's body position, or other factors. In some implementations, acquiring measurements during a contemporaneous time period (or very nearly the same time period) may ensure that the measurements are taken under the same conditions. Therefore, in some implementations, if the need for measurements under similar conditions may be relaxed or eliminated, then the $P_IO_2$, $P_AO_2$, $P_ACO_2$ and $SpO_2$ measurements may be acquired at non-contemporaneous times (e.g., one or all three of the measurements may be obtained at different times, with times in between measurements, at consecutive times, etc.)

In various implementations, the gas partial pressure measurement at block 304 may comprise detecting a partial pressure of only exhaled $CO_2$, only exhaled $O_2$, or both exhaled $O_2$ and exhaled $CO_2$. In some implementations, other gases (e.g., $N_2$ or others) may be measured in addition to or instead of $CO_2$ and $O_2$.

In some implementations, gas partial pressure measurements may be continuously collected by digitally sampling analog gas analyzer signals at a desired digital sampling rate, and storing the digital samples in a volatile or non-volatile memory device. The digital sampling step may be omitted if the analyzers output digital data. In some implementations, continuous gas partial pressure measurement data may be collected during a time period that may begin when the gas exchange test begins, when steady-state breathing is detected, or at some other time during the gas exchange test. The time period for continuous gas partial pressure measurement data collection may end when oximonitor system 100 detects that the patient has stopped breathing through the steady-state breathing tube 112 or at another time after the gas exchange test has begun.

In other implementations, gas partial pressure measurements may be instantaneous measurements taken at specific intervals. Alternately, one or more instantaneous gas partial pressure measurements may be taken at a pre-determined time after determining that steady-state breathing has been achieved, or at any other specified time after the gas exchange test begins.

Similarly, the oxygen saturation measurements may be continuous over a time period (e.g., the same time period as a continuous measurement of gas partial pressure(s)) or instantaneous at one or more desired times. In some implementations, oxygen saturation measurements may be taken substantially continuously from a starting time after the gas exchange test begins until a pulse oximetry test end time.

In some implementations, oximonitor system 100 may be configured to determine a pulse oximetry test end time automatically based on an analysis of the collected oxygen saturation sample data. In some implementations, oximonitor system 100 may be configured to indicate when a pulse oximetry test end time has been reached by illuminating a light of a particular color (e.g., a green light) or by displaying a numeric, textual, or symbolic message on the display screen.

At block 306 of the process 300, oximonitor system 100 may obtain an end-tidal value of the partial pressure of carbon dioxide in the exhaled air based on continuous and/or instantaneous digital data samples. In some implementations, the system may also determine an end-tidal value of the partial pressure of oxygen in the exhaled air.

FIG. 4A illustrates various phases of breathing showing partial pressure of $CO_2$ for normal and abnormal (e.g., obstructed) breathing. The dotted line curve represents a $PCO_2$ waveform representing normal un-obstructed breathing for an "average" person based on clinical data (e.g., from population studies), which may be treated as a baseline against which patient measurements may be compared. Different clinical baselines may be used based on a patient's age, condition, or other factors. The solid-line curve represents a $PCO_2$ waveform showing breathing that is obstructed, such as by asthma, emphysema, or other form of COPD.

Determination of an end-tidal value may be understood with reference to FIG. 4A and FIG. 4B, which illustrates a graph of example $O_2$ and $CO_2$ partial pressure data collected over a period of time. The dotted-line curve of FIG. 4B represents a partial pressure of exhaled $CO_2$. The solid-line curve represents a partial pressure of exhaled oxygen. Both curves are shown during a number of inspiration/expiration breathing cycles. During each expiration cycle, $PCO_2$ and $PO_2$ rise up, come to a plateau (which may have a rising slope), and then fall as the expiration cycle ends.

As used herein, the phrase "end-tidal value" refers to the value of a measured variable at the end of an expiration cycle (i.e., at the completion of exhalation of a tidal volume). Therefore, in some implementations, an end-tidal value of $CO_2$ or $O_2$ may be determined from a series of data points by identifying the end-of-cycle point in each cycle. For example, in FIG. 4B a peak 410 at the end of each exhale cycle is indicated by a circle, corresponding to end-tidal $CO_2$. In some implementations, the peak 410 at the end of each exhale cycle may be identified by identifying a local maximum partial pressure value during each cycle. Alternatively, the peak 410 at the end of each exhale cycle may be identified by detecting a sudden change of slope, and identifying a peak immediately preceding the slope change. In some implementations, a combination of both peak-detection and slope-change-detection may be used to identify a local end-tidal value for each cycle. The same or similar techniques may also be used for determining a local end-tidal value of $O_2$ for each expiration cycle, e.g., as illustrated by circles 412 at the bottom of each $O_2$ cycle.

In some implementations, local end-tidal values may be obtained for a plurality of cycles, and the local results may be averaged to obtain normalized end-tidal value. Alternatively, a normalized end-tidal value may be obtained based on a maximum of multiple cycles, a minimum of multiple cycles, a median of multiple cycles, a mean (average) of multiple cycles or other normalization method. In some implementations, a normalized end-tidal value may be obtained based on a pre-determined number of breathing cycles (e.g., 2, 3, 4, 5, 6 or more cycles). In other implementations, a normalized end-tidal value may be obtained based on an arbitrary number of cycles occurring within a predetermined time duration 420. In some implementations, a normalized end-tidal value may be the end-tidal value used in calculations, the end-tidal value used for reporting directly on a display screen, and/or the end-tidal value stored in a memory device. The same or similar techniques may be used for determining normalized values of $P_AO_2$ and $P_ACO_2$.

At block 326 of the process 300, oximonitor system 100 may calculate a partial pressure of arterial oxygen based on the end tidal partial pressure of $CO_2$ ($PETCO_2$) determined at block 320 and the oxygen saturation ($SpO_2$) measured at block 316. In various implementations, the value of $SpO_2$ used in the calculation at block 316 may be a normalized value obtained from a plurality of data points obtained over a pre-determined time period (e.g., an average, a maximum, a minimum, a median, or other normalization), or the value of $SpO_2$ used in the calculation at block 316 an instantaneous value. Additional details of the calculation performed at block 326 are described below.

In some implementations, the gas analyzers may be used to collect samples of ambient air at a time when a patient is not breathing through the steady-state breathing tube. Such ambient air samples may be analyzed to determine partial pressure of $O_2$, $CO_2$, and/or other gases present in ambient air. Some gas sensors may be capable of automatically adjusting for changes in ambient air pressure (e.g., due to altitude or other variations). For example, some gas sensors may detect a difference in a concentration (or quantity) of a target gas in an exhaled sample as compared with the concentration (or quantity) of the target gas in ambient air. In some implementations (e.g., in systems configured for use in high altitude applications where ambient pressure is expected to be lower than at sea level), oximonitor system 100 may be configured to measure a total ambient air pressure using an onboard barometric pressure gauge. The measured ambient air pressure may be used to adjust gas partial pressure measurements taken during the gas exchange test based on generally accepted values describing the composition of atmospheric air at various altitudes. In some implementations, ambient air partial pressure measurement values may be displayed on an output device whether or not they are used to adjust gas exchange test values.

In various implementations, a forced expiratory breath test may include any of various testing procedures generally known as spirometry. The process for performing a forced expiratory breath test may vary slightly depending on the equipment used. Generally, the patient may be asked to take the deepest breath they can, and then exhale into pulmonary mechanics flow tube 116 as hard as possible, for as long as possible (preferably at least 6 seconds, in some implementations). As the patient exhales, the pulmonary mechanics measurement controller may monitor and record a volumetric flow rate of exhaled (and/or inhaled) air and elapsed time.

This process may be directly followed by instructing the patient to rapidly inhale. This may be useful, for example, when assessing possible upper airway obstruction. In some implementations, the forced expiratory breath test may be beneficially performed immediately following the gas exchange test described herein.

During the forced expiratory breath test(s), soft nose clips 124 may be used to prevent air escaping through the nose. Filter mouthpieces may be used to prevent the spread of microorganisms.

Any of various parameters may be collected, determined, stored, and/or presented on an output display. Such parameters may include known spirometry parameters such as forced vital capacity measure (FVC, which is the total volume of air expired during the forced expiratory test); forced expiratory volume in one second ($FEV_1$); a ratio of $FEV_1/FVC$ ($FEV_1\%$); a forced expiratory flow rate (FEF) taken at discrete times, continuously, or at pre-determined intervals; forced inspiratory flow rate; maximal expiratory flow (MEF, which is the peak of expiratory flow taken from a flow-volume curve); peak expiratory flow rate (PEFR); or others. Numerical and/or graphical representations of these or other measures may be displayed and/or stored for later viewing.

In various implementations, oximonitor system 100 may include survey software configured to collect user input in response to a series of questions about the patient's symptoms. Long term patient's symptoms are very useful in tracking the progression of various breathing-related disorders. Oximonitor system 100 may be configured to encourage patients to log their daily symptoms over several weeks, by answering a few simple questions. For example, the questions may include: Is your cough worse than it was yesterday? Is your sputum or phlegm worse than yesterday? How much sputum are you producing daily? Has your breathing worsened since yesterday? (among other questions or variations on these questions.) In some implementations, oximonitor system 100 may also ask questions regarding the patient's exercise tolerance. For example, oximonitor system 100 may prompt the patient to indicate whether their ability to walk non-stop is better or worse than the previous day, typically known as an exercise tolerance test in clinical context. Collected answers to these or similar yes or no questions may accurately show whether a condition is improving or worsening over time.

In some implementations, instead of or in addition to questions demanding a "yes" or "no" response, oximonitor system 100 may be configured to present one or more questions that may be answered with a variable response, such as a variable value on a scale (e.g., "How bad is your cough on a scale of 1 to 5?") In other implementations, some questions may be presented in response to a patient providing a particular answer to one or more previous questions.

For example, if a patient answers "yes" when prompted whether their sputum is worse than yesterday, oximonitor system 100 may be configured to follow up with a question requesting the patient to rate the quantity of sputum on a numeric or other scale.

In various implementations, oximonitor system 100 may be configured to prompt a patient for answers to symptom tracking questions at regular time intervals.

In various implementations, oximonitor system 100 may be configured to prompt a patient for answers to symptom tracking questions within a pre-determined time following another test performed by oximonitor system 100 (e.g., a gas exchange test or a pulmonary mechanics test). Alternatively, oximonitor system 100 may be configured to prompt a patient for answers to symptom tracking questions no sooner than a pre-determined time following another test performed by oximonitor system 100. For example, oximonitor system 100 may produce an audible or visible prompt indicating that a patient (or a patient's caregiver) should input answers to the symptom questions.

In some implementations, oximonitor system 100 may be configured to prompt a patient for answers to symptom tracking questions at regular time intervals, such as once per day (e.g., at the same time every 24 hours), twice a day, or at any other frequency or time interval. In some implementations, a patient or other user may set a reminder interval to a desired frequency or time interval.

In some implementations, oximonitor system 100 may be configured to prompt a patient for answers to symptom tracking questions at shorter intervals if answers are not provided within a pre-determined time of an initial prompt. For example, oximonitor system 100 may be configured to "nag" the patient or other user until answers are provided.

In some implementations, oximonitor system 100 may be configured to add questions, remove questions, or modify questions based on results of a gas exchange test, a pulmonary mechanics test, or other tests.

In various implementations of the present disclosure, arterial blood oxygen content (partial pressure) may be reasonably accurately estimated based on the results of non-invasive tests as described herein.

The relationship between blood oxygen saturation ($SpO_2$) and arterial blood oxygen partial pressure ($P_aO_2$) is well represented by the Oxygen-hemoglobin Dissociation Curve. Mathematical representation of this relationship may be described by the Bohr effect which states that hemoglobin's oxygen binding affinity is inversely related to acidity and concentration of carbon dioxide in the blood. For example, increase in $CO_2$ decreases pH, resulting in hemoglobin proteins releasing their load of oxygen. It was experimentally discovered by the Danish scientist, Bohr, that oxygen binding curve was sigmoidal in shape. The Bohr effect is further advanced by the Hill equation used in biochemistry that mathematically describes oxygen binding to hemoglobin. Mathematical representation could use a "Fractional occupancy" term, Y which is a protein receptor (E.g. hemoglobin) with a given molecule (E.g. oxygen), which is defined as the quantity of molecule bound binding sites divided by the total quantity of molecule binding sites. If Y=0, it is not saturated and if Y=1, it is completely saturated as follows:

$$Y = \frac{\text{bound sites}}{(\text{bound sites} + \text{unbound sites})}$$

This cooperative binding to a multi-site protein like hemoglobin increases affinity for the oxygen molecule and has been known as the Hill equation with the following form:

$$\overline{Y} = \frac{K*[X]^n}{1+K*[X]^n} = \frac{[X]^n}{K+[X]^n}$$

Where "n" is the "Hill coefficient," [X] denotes molecular concentration, K denotes an empirical dissociation constant. If n>1, the cooperative binding is positive. Although this oxygen-hemoglobin relationship is a non-linear relationship, it is not fixed but is individualized, meaning it shifts depending on the partial pressure of $CO_2$ in the blood, pH of the blood, temperature, and presence of DPG (2,3-DPG is an inorganic phosphate) produced in red blood cells.

In various implementations of the present disclosure, the partial pressure of arterial oxygen ($P_aO_2$, expressed in units of mmHg) may be approximated based on measurements of atmospheric pressure, inspired oxygen, expired carbon dioxide, other physiologic variables, and peripheral arterial blood oxygen saturation ($SpO_2$, expressed in decimal form), using a relationship derived from the oxygen-hemoglobin dissociation curve and the above assumptions.

Individual adjustment of the oxygen-hemoglobin dissociation curve may be made to arrive at the proper arterial partial pressure ($P_aO_2$) based on differing physiologic variables. In various implementations of the present disclosure, the partial pressure of arterial oxygen ($P_aO_2$, expressed in units of mmHg) may be approximated based on direct measurements of several measured parameters using the relationship shown in Equation 2 below.

$$P_aO_2 = A^{n}*(S_PO_2/1-S_PO_2)^{1/n} \quad \text{(Equation 2)}$$

Where: n=is the Hill coefficient that may range from about 2.3 to 3.0, where 2.7 may be preferred, and A is obtained from the relationship of Equation 3. Severinghaus (1979) and others have shown that this equation given above fits the oxygen dissociation curve closely. For example, between the saturations of 94 and 30%, the error in the calculated PO2 is less than 5 mmHg.

$$A = C_0 + C_1*V_1 + C_2*V_2 + C_3*V_3 + C_4*V_4 + C_5*V_5 + C_6*V_6 + C_7*V_7 \quad \text{(Equation 3)}$$

Where $C_0$ is an experimentally derived constant, and $C_1$, $C_2$, $C_3$, $C_4$, $C_5$, $C_6$, and $C_7$ are coefficients experimentally derived and/or referenced from published research findings. $V_1$-$V_7$ are input variables directly measured or derived from direct measurements at each session. The variables $V_1$-$V_7$ correspond to the measurable metrics shown in Table 1 below:

TABLE 1

Example variables

| EQ2 variable | Metric | Description | Metric type |
|---|---|---|---|
| $V_1$ | Pbar | Atmospheric pressure, in mm Hg. (sea level = 760 mmHg) | Measured |
| $V_2$ | $P_IO_2$ | Inspired oxygen partial pressure, mmHg | Measured |
| $V_3$ | $SpO_2$ | Oxygen saturation value, in % | Measured |
| $V_4$ | $PCO_2$ | Expired end tidal carbon dioxide level, in mm Hg | Measured |
| $V_5$ | pH | The acid-base balance of blood (typically 7.4) | Derived |
| $V_6$ | T | The body temperature (typically 37 C.) | Measured |

TABLE 1-continued

Example variables

| EQ2 variable | Metric | Description | Metric type |
|---|---|---|---|
| $V_7$ | DPG | 2,3-DPG: An inorganic phosphate produced in red cells | Derived |

For example, to account for the effects of changes in oxygen affinity of hemoglobin only by $PCO_2$, then A can be expressed as P50 and its relationship to $PCO_2$ can be expressed, according to the Kelman sub-routines, as A=B1+B2*$PCO_2$, where B1 and B2 are constants derived from Kelman sub-routines, and may be adjusted from experimental data assuming that the base excess is zero. In various implementations, the constant B1 may have a value of between about 16.5 and about 19.0. For example, the constant B1 may have a value of 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, or 18.5. In some implementations, the constant B1 may have a value less than about 16.5 or greater than about 18.5.

In various implementations, the constant B2 may have a value of between about 0.210 and about 0.230. For instance, the constant B2 may have a value of 0.210, 0.211, 0.212, 0.213, 0.214, 0.215, 0.216, 0.217, 0.218, 0.219, 0.220, 0.221, 0.222, 0.223, 0.224, 0.225, 0.226, 0.227, 0.228, 0.229, or 0.230. In some implementations, the constant B2 may have a value less than about 0.210 or greater than about 0.230.

The end-tidal PCO2 is used for the arterial value. The effects of changes in the PCO2 on the P50 are relatively small. For example, an increase in PCO2 from 40 to 50 mmHg results in a change in P50 of only about 2 mm Hg. In patients with severe COPD, the end-tidal PCO2 will be appreciably lower than the arterial value because of the contribution of alveolar dead space. But this affinity of hemoglobin can be affected by other factors which can be derived computationally using directly measured values.

Figure 3C:
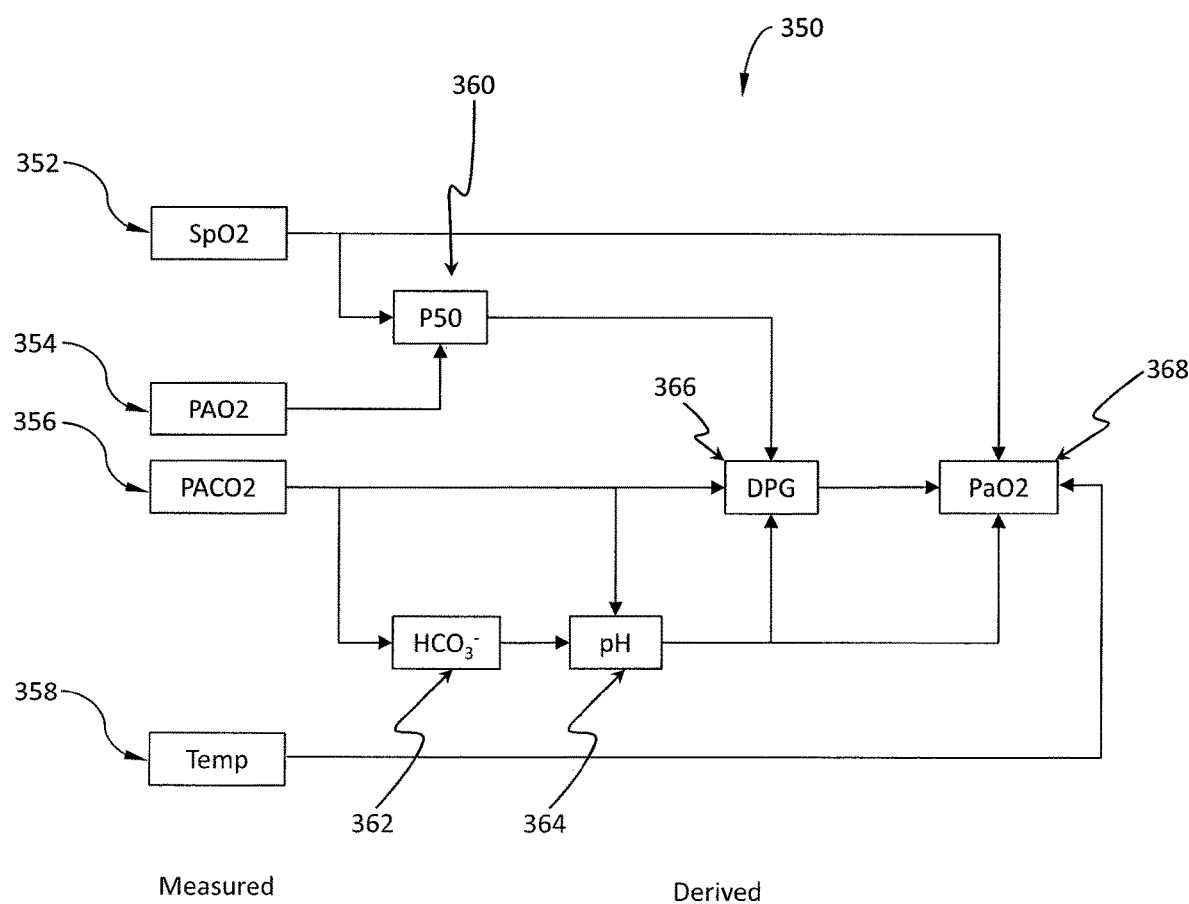
FIG. 3C is a detailed computational flow diagram illustrating an exemplary process for calculating gas exchange parameters, according to one implementation of the present disclosure.

To calculate the derived values, the software may implement the calculation algorithm 350 in FIG. 3C. The hardware components of the device may measure $SpO_2$, $P_AO_2$, $P_ACO_2$, and temperature. Once these values are measured, they are used to compute other variables that could be considered as intermediate parameters impacting final $PO_2$ computation. The calculation of A (P50) 360 depends on the measurement of $SpO_2$ 352 and the measurement of $P_AO_2$ 354. The calculation of $HCO_3^-$ 362 depends on the measurement of $P_ACO_2$ 356. The calculation of pH 364 depends on the calculation of $HCO_3^-$ and the measurement of $P_ACO_2$. The calculation of DPG 366 depends on the calculation of P50, the calculation of pH, and the measurement of $P_ACO_2$. Finally, the calculation of $P_AO_2$ 368 depends on the calculation of DPG, the calculation of pH, the measurement of $SpO_2$, and the measurement of temperature 358.

The above calculations are described as follows, where in the calculation of bicarbonate, it follows that:

$$\Delta PACO2 = PACO2 - [PACO2]$$

$$\Delta HCO_3^- = HCO_3^- - [HCO_3^-]$$

In addition to these relationships, some have established $\Delta PACO2$ and $\Delta HCO_3^-$ have the following proportional relationship, where the $\beta$ is varied by disease type:

$$\Delta PACO2 = \beta * \Delta HCO_3^-$$

Algebraic manipulation of the above three relations gives Equation 3.1:

$$\Delta PACO2 = \beta * \Delta HCO_3^- \quad \text{(Equation 3.1)}$$

$$\Delta HCO_3^- = HCO_3^- - [HCO_3^-] = \frac{\Delta PACO2}{\beta}$$

$$HCO_3^- = [HCO_3^-] + \frac{\Delta PACO2}{\beta}$$

The table below describes known values and ranges for the variables in Equation 3.1.

| Name | Definition | Range |
|---|---|---|
| $[P_ACO_2]$ | Standard alveolar PCO2 value | 40 |
| $[HCO_3^-]$ | Standard bicarbonate value | 24 |
| $\beta$ | Relation coefficient | −5 to 5 |

In some implementations of the pH calculation, the expression for $HCO_3^-$ in Equation 3.1 is inserted into the Henderson-Hasselbalch equation, yielding the pH value ($pK_A$ is the negative logarithm of the acid dissociation constant and it has a typical value of 6.1).

$$pH = pK_A + \log \frac{HCO_3^-}{PACO2 * 0.03} \quad \text{(Equation 3.2)}$$

In various implementations, the P50 calculation uses a Hill factor of 2.7, and the P50 can be described as a function of $P_AO_2$ and $SpO_2$.

$$\log P50 = \log PAO2 - \left[\log\left(\frac{SpO2}{100 - SpO2}\right)\right] / 2.7 \quad \text{(Equation 3.3)}$$

In some implementations, where the value of hemoglobin is defined as normal since it is unattainable form the measured parameters, the DPG calculation can be expressed as following:

$$DPG = Hb * 10^{\left[\frac{\log P50 - (\mu_3(pH)*PACO2 + \mu_4(pH))}{\mu_1(pH)*PACO2 + \mu_2(pH)}\right]}, \quad \text{(Equation 3.4)}$$

where the pH and P50 may be used from Equation 3.2 and 3.3.

A table of typical values for the unmeasured constants is provided below.

| Name | Definition | Range |
|---|---|---|
| $\mu_1$ (pH) | Function of pH | −0.70e−3 to −0.13e−2 |
| $\mu_2$ (pH) | Function of pH | 0.3 to 0.4 |
| $\mu_3$ (pH) | Function of pH | 0.3e−3 to 0.9e−3 |
| $\mu_4$ (pH) | Function of pH | 1.2 to 1.6 |
| Hb | Hemoglobin (g/L) | 164 |

In some implementations, the parameter may be expressed as a fraction or converted to a percentage parameter between zero percent and hundred percent. However, in other implementations, the parameter may be logarithmic number of variable input (Vi). In some implementations, the software processes the output and use any single or multiple variables to reduce error rate or variability of the data against theoretical baseline.

In some implementations, the parameter input may use default values already included in the software or determined using an ABG test, and values may be manually or automatically entered into an oximonitor system based on the results of an ABG test or other test information if available. In some implementations, non-physiological parameters may also be measured using equipment independent of the oximonitor system, and such independently measured parameters may be manually or automatically input into the oximonitor system.

With the sigmoidal oxygen-hemoglobin dissociation curve, a large partial pressure difference between the alveolar gas and blood continues to exist when most of the $O_2$ has been transferred. This in turn slows down the diffusion process, as explained by the sigmoidal nature of the oxygen-hemoglobin dissociation curve. At sea level, where atmospheric pressure is 760 mm Hg and in room air setting, the normal value for $PO_2$ in young adults averages about 95 mmHg, and ranges from about 85 to about 100 mmHg in $P_aO_2$ (or 95% or higher in saturation, $SpO_2$). This expected normal value of arterial $P_aO_2$ decreases steadily with age, so expected average value is approximately 85 mmHg at age 60 years. The oxygen-hemoglobin dissociation curve may be individualized per person by accounting for physiologic changes. For instance, the dissociation curve is shifted to right by increase in DPG (2,3-diphosphoglycerate) inside the red cells, temperature, $PCO_2$ and increased $H^+$ concentration (which decreases pH) as shown in FIG. 4C. In some implementations, each additional variable may be separately added to the algorithm 330 in FIG. 3B to enhance $P_aO_2$ calculation 326 until data variability is observed by the software process to be within an acceptable range as measured by two standard deviations of the computed data set against expected theoretical value 328. In one implementation, the $P_aO_2$ calculation step 326 starts with $V_4$ as input value and computes, if initially computed value falls within 1 sigma but less than 2 sigma, then the software improves by adding additional variables in the order of $V_1$, $V_2$, $V_5$, $V_6$ then $V_7$ until the calculated value falls within two (2) sigma value and stops the routine.

If measured value is not available, then software takes the default value as provided by the software 326 or using built in look up table.

Each single breath may produce corresponding respiratory measures. Continuing such measurements and calculations over a period of many breathing cycles may produce a "continuous" time-varying estimations of $P_aO_2$. The term "continuous" is used to describe such consecutive calculated $P_aO_2$ values despite the elapsed time in between each end-tidal value on which each $P_aO_2$ value is based. Because the time of each end-tidal value is known based on a clock time of controller 210 or other processor, the $P_aO_2$ values may be plotted on a continuous waveform graph. In some implementations, lines may be displayed between each $P_aO_2$ value on such a continuous waveform graph. Such connecting lines may be linear or curved as desired to illustrate trends over time.

In some implementations, Equation 2 may need to be modified to reflect case of anemic patient. Anemia is a condition marked by a deficiency of red blood cells or of hemoglobin in the blood and this may result in left shifting of the dissociation curve. The left shifting of the curve affects the binding affinity for oxygen.

Anemic patient with abnormal forms of hemoglobin, may have normal lungs and arterial $P_aO_2$ of 100 mm Hg, but the patient's total oxygen binding capacity will be reduced from 20.8 ml*100 ml$^{-1}$ to 13.8 ml 100 ml$^{-1}$ there by lowering the total oxygen content of the blood. In this case, this patient's $O_2$ saturation may appear normal at 97.5% (at normal pH, $pCO_2$, and temperature), but the $O_2$ combined with hemoglobin will be lower than normal of perhaps 13.5 ml*100 ml$^{-1}$. The oxygen concentration of blood (expressed as $CaO_2$ in ml $O_2$*100 ml$^{-1}$ blood) is given by the following relationship:

$$CaO_2 = \left(1.39 * Hb * \frac{Sat}{100}\right) + .003 P_aO_2,$$

Where Hb is the hemoglobin concentration in grams per 100 ml of blood.

A reduced Hb concentration will appear as purple, and produce a clinical manifestation of cyanosis. This is not always a reliable indicator because its recognition depends on multiple variables, such as skin pigmentation and lighting of the room. In the case of anemic patients, Equation 2 may be modified to correct the values using the above relationship assuming Hb concentration is available and is provided.

Additionally, the oximonitor system 100 may determine a respiratory rate by counting the number of breathing cycles that occur within a particular period of time. Respiratory rate is typically reported in units of breaths per minute, so in some implementations, an oximonitor system 100 may count the number of complete breathing cycles that occur within a sixty-second period of time. Alternatively, breathing cycles may be counted during known periods of time shorter or longer than 60 seconds and the total count may be mathematically adjusted to obtain a breaths-per-minute respiratory rate value.

As used herein, the term "oxygen deficit" refers to a quantitative metric describing the gas exchange efficiency of a patient's lungs based on a difference between the partial pressure of oxygen in the patient's alveoli (referred to herein as "alveolar oxygen") and the partial pressure of oxygen in the patient's peripheral arteries (referred to herein as "arterial oxygen"). As used herein, oxygen deficit provides a single numerical measure of inefficiency of the patient's lungs and body at taking up oxygen from inspired air into the blood and to transport oxygen to the tissue. A larger oxygen deficit value indicates a lower oxygen exchange efficiency (i.e., a greater oxygen exchange inefficiency). In equation form, oxygen deficit (D) is the difference between a measured quantity of alveolar oxygen ($P_AO_2$) and a measured quantity of arterial oxygen ($P_aO_2$):

$$D = P_AO_2 - P_aO_2 \tag{Equation 4}$$

Among medical professionals, the difference between alveolar oxygen ($P_AO_2$) and arterial oxygen ($P_aO_2$) is known as the "Alveolar-arterial gradient," or the "A-a" gradient. The A-a gradient may be determined using an ABG test and the "alveolar gas equation," which assumes a fixed relationship between alveolar oxygen levels and various quantities measurable with an ABG test. The term oxygen deficit (or "$O_2$ deficit") is used herein to distinguish between the blood-test-based A-a gradient and the breath-based estimates obtained with an oximonitor system 100.

Figure 4E:
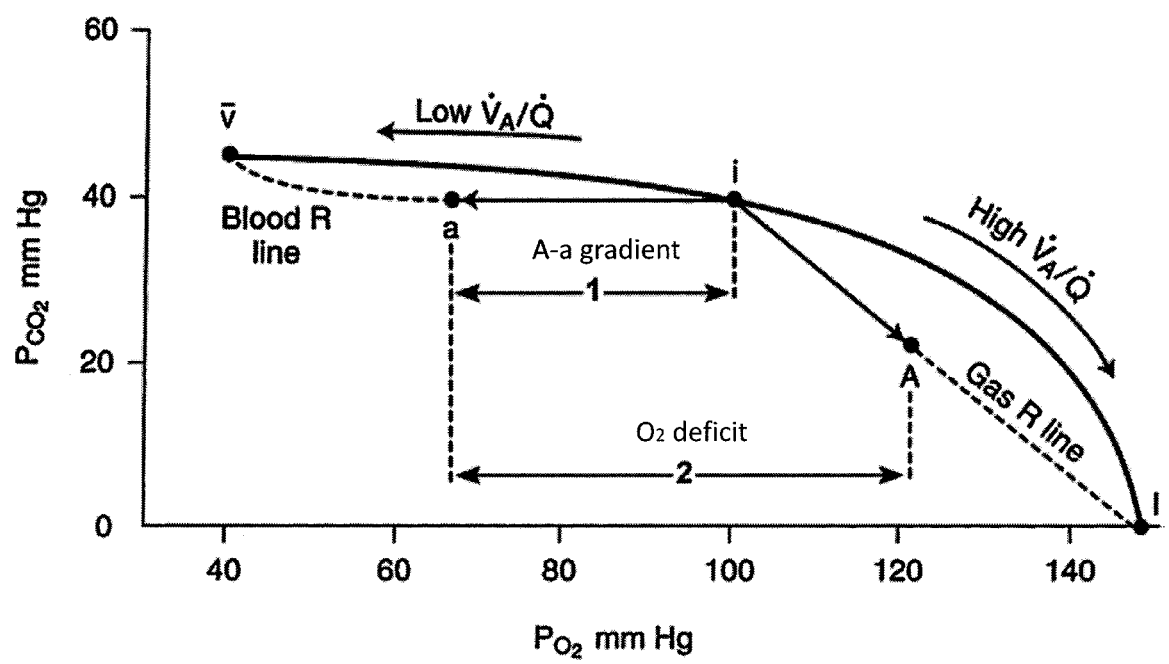
FIG. 4E is an oxygen-carbon dioxide diagram showing the ventilation-perfusion ratio line, according to one implementation of the present disclosure.

The oxygen-carbon dioxide diagram in FIG. 4E shows the gas composition of lung units for all ventilation-perfusion ratios from zero, the value for mixed venous blood, to infinity, the value of inspired gas (Rahn and Fenn, 1955). For simplification, the diagram shows the inspired $PO_2$ and $PCO_2$ to be those of air at sea level, and the mixed venous point is that for the normal lung with a $PO_2$ of 40 and $PCO_2$ of 45 mmHg. The VA/Q line shows all possible values for the $PO_2$ and $PCO_2$ and lung units throughout the lung.

The derivation numbered 1 in FIG. 4E ("A-a gradient") uses the measured arterial $PO_2$ and $PCO_2$ from an arterial blood gas sample (labeled "a"). However, the alveolar values are not known from ABG measurements. Instead, the so-called ideal alveolar $PO_2$ is calculated. The ideal alveolar gas composition is that which the lung would have if there were no ventilation-perfusion inequality and the respiratory exchange ratio was the same as the actual lung (labeled "i"). This calculation is done by taking the $PCO_2$ of the arterial sample, and by assuming that the $PCO_2$ of ideal alveolar gas is the same. This is a reasonable assumption because the line joining the alveolar ideal point and the arterial point is almost horizontal as shown in the figure. The alveolar gas equation is then used to calculate the ideal alveolar $PO_2$ using the inspired $PO_2$ and the measured or assumed respiratory exchange ratio.

Now turning to the derivation numbered 2 in FIG. 4E ("$O_2$ deficit"), we have the arterial $PO_2$ on the left, although this is calculated as described above from the $SpO_2$. On the right we have the alveolar $PO_2$, which is given by the end-tidal value (labeled "A"). The difference between alveolar and arterial $PO_2$ measured by the new device is larger than the traditional $PO_2$ difference between arterial blood and ideal alveolar gas, previously defined as the "A-a gradient."

This new value shown in the derivation numbered 2 in FIG. 4E may be more informative than the traditional ABG-derived value shown in number 1. The "A-a gradient" depends heavily on the contribution of lung units with low ventilation-perfusion ratios. By contrast, the "$O_2$ deficit" shown in derivation numbered 2 in FIG. 4E includes both the contributions of lung units with low ventilation-perfusion ratios, and those with abnormally high ratios. It is therefore a more comprehensive metric for the distribution of ventilation-perfusion ratios in the lung.

Some implementations may further compare breath-based measurement of oxygen deficit ($P_AO_2-P_aO_2$) to Alveolar-arterial gradient (estimated $P_AO2-P_aO_2$ from arterial blood gas test), and display both points along the ventilation-perfusion line and highlighting low VA/Q (ventilation perfusion inequality) to high VA/Q compared against ideal point (i) where there is no ventilation and perfusion inequality of the lung. The difference between the two values and magnitude of difference indicates the contribution from either ventilation (air flow) to perfusion (blood flow) based disorders from high VA/Q units of the lung, such as those found in mixed cardio pulmonary conditions.

In some implementations, the system further compares oxygen deficit ($P_AO_2-P_aO_2$) to Alveolar-arterial gradient (estimated $P_AO2-P_aO_2$ from arterial blood gas test) and RQ slope, and visually indicates the direction of inefficiency of lung to conduct gas exchange contributed by either ventilation (air flow) or perfusion (blood flow) or mixed case.

As with $P_ACO_2$ values, the relationship of Equation 4 may produce one value of $O_2$Deficit for each breathing cycle. The $O_2$ deficit may also be displayed as a continuous waveform over time with or without connecting lines which may be linear or curved.

In various implementations, oximonitor system 100 may be configured to collect data obtained from each of the above-described tests over time. Oximonitor system 100 may include an internal storage device for storing test result data and survey responses on the device. Additionally, or alternatively the oximonitor system 100 may be configured to transmit test data and survey responses over a communications network for storage or use at a remote location. For example, oximonitor system 100 may include electronics and software for communicating over WiFi, Bluetooth, Ethernet, SMS, WAP, HTML, cellular networks, or any other wired or wireless networking communication protocol. Data stored on a remote server may be accessed, viewed, and used by physicians for diagnosing patients or monitoring patients' conditions.

In various implementations, test data and survey responses may be displayed on the display screen of oximonitor system 100 or on a remote display. Data may be displayed alphanumerically, graphically, or as a combination of graphics and alphanumeric text. In some implementations, test data and/or survey response data may be displayed graphically and/or alphanumerically immediately after a test is completed, or at any time that historical data is requested. Data may be displayed to show time series of metrics over time, which may illustrate short-term trends, long-term trends, comparisons to population averages, or various other metrics.

For example, in some implementations, measured $CO_2$ and $O_2$ partial pressure values may be displayed in real-time (or at as near to real-time as possible) while a gas exchange test is being performed. In some implementations, either or both of the $CO_2$ and $O_2$ partial pressure curves of FIG. 4B may be displayed during a gas exchange test or afterwards. In some implementations, a normalized value or an analysis result such as end-tidal value may be displayed as text or as a horizontal line.

Figure 5A:
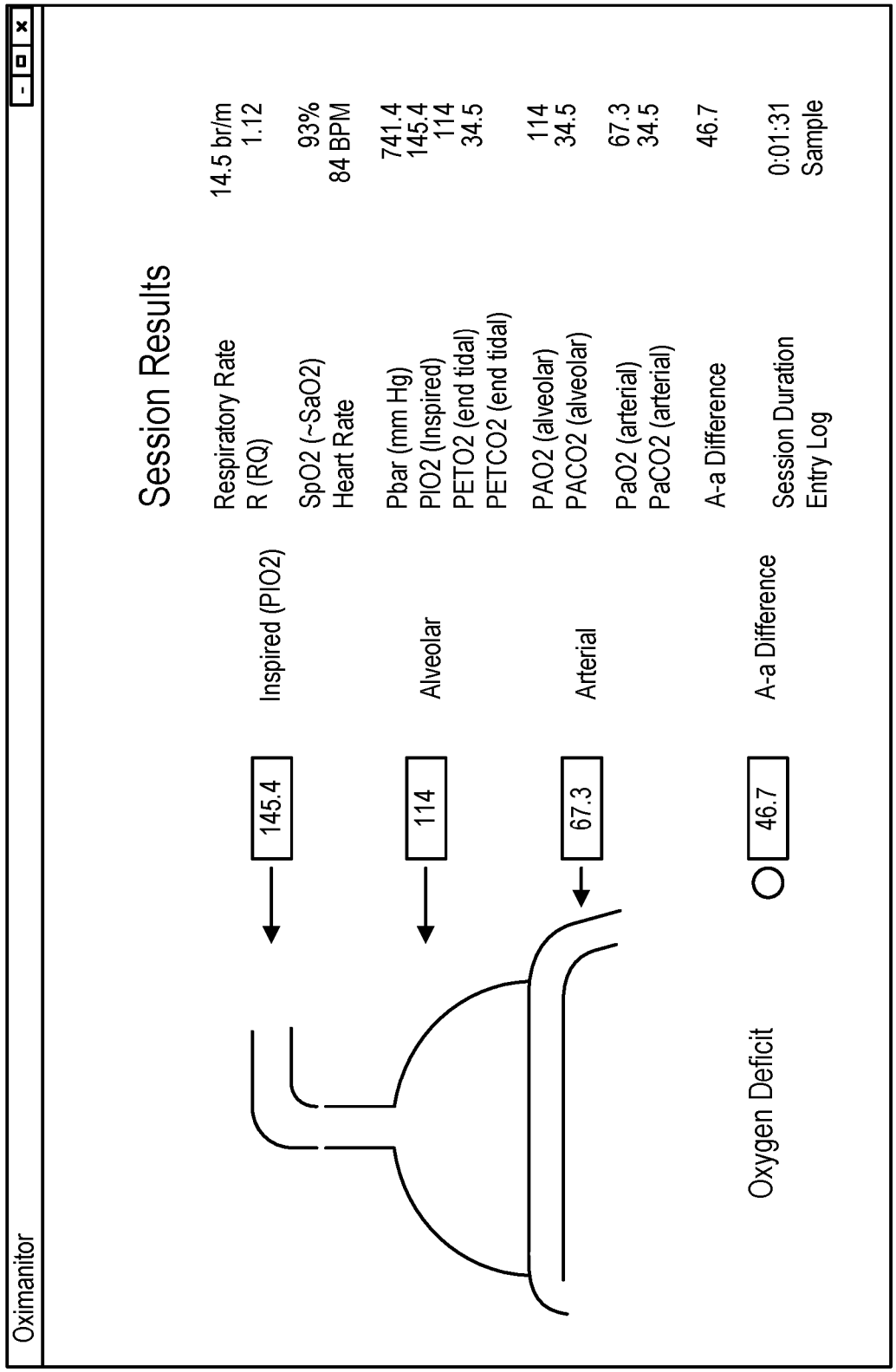
FIG. 5A is a diagram illustrating an example of output data displayed based on results of a gas exchange test using an oximonitor device, according to one implementation of the present disclosure.

FIG. 5A illustrates an example of output that may be displayed following a gas exchange test. The graphic on the left side of the display schematically represents the gas exchange system, beginning with the lungs (indicated by the "inspired" value), proceeding through alveoli, and ending with the peripheral arterial vasculature. The partial pressure of ambient air indicated by the "inspired" value may be an assumed value based on a detected altitude or atmospheric pressure, or may be a directly measured value based on a sample of ambient air. The "alveolar" value may be the measured partial pressure of alveolar oxygen. The "arterial" value may be the value calculated using the relationship of Equation 2 which can be referred to as the "Breath $P_aO_2$ Relation." The "oxygen deficit" may be the value calculated using Equation 4 described above. In some implementations, the display of the oxygen deficit value may be made to blink if the value exceeds a baseline value established for a patient.

In some implementations, the system may measure $P_AO_2$, $P_ACO_2$, and $SpO_2$, and in order to calculate $P_aO_2$ and RQ. It may also compare breath-based measurement of oxygen deficit ($P_AO_2-P_aO_2$) to Alveolar-arterial gradient (estimated $P_AO2-P_aO_2$ from arterial blood gas test). Using these parameters, it may determine whether a patient has a ventilation or perfusion based gas exchange inefficiency. The results of that may be indicated by visual cues, such as blinking or highlighting, in the image on the left of FIG. 5A. If a ventilation defect is determined as the physiological cause of the gas exchange inefficiency, the upper portion of the image on the left (representing the lungs) in FIG. 5A may be highlighted in one of various colors, or it may blink to notify physicians of the main source of the deficiency. On the other hand, if the system determines that perfusion is the main source of the inefficiency, the system may either highlight the lower part of the image on the left side of FIG.

5A (the part that symbolizes the blood and the arteries) with one of various colors or cause that part of the image to blink. This may allow physicians and practitioners to more easily detect the type of respiratory problem a patient may be experiencing because the system may visually facilitate the determination of the origin of any ventilation-perfusion inequality if present.

In various implementations, displayed or recorded values of $P_AO_2$, $P_ACO_2$, $P_aO_2$, $P_aCO_2$, or oxygen deficit may be end-tidal values from a single breathing cycle or an average value based on end-tidal values from several breathing cycles. In one example, values of $P_ACO_2$ and $SpO_2$ may be obtained during a period defined by a pre-determined number of breathing cycles (e.g., 2 to 10 or more) or as a pre-determined period of time (e.g., 30 seconds to a minute or more), then a value of $P_aO_2$ may be calculated for each breathing cycle using the Breath $P_aO_2$ Relation, and the multiple $P_aO_2$ values may be averaged to obtain an average $P_aO_2$ value for the period. In another example, values of $P_ACO_2$ and $SpO_2$ may be obtained during a period (e.g., 2 to 10 or more breathing cycles or 30 seconds to a minute or more), and an average $P_ACO_2$ value for the period may be obtained by averaging the end-tidal values from the breathing cycles during the period. The average $P_ACO_2$ value may then be used to obtain an average value of $P_aO_2$ for the period. Using either method, average values may be regularly updated for a trailing fixed-length period. Similarly, values of oxygen deficit may be calculated and updated as an average over a trailing period of time or breathing cycles.

Figure 5B:
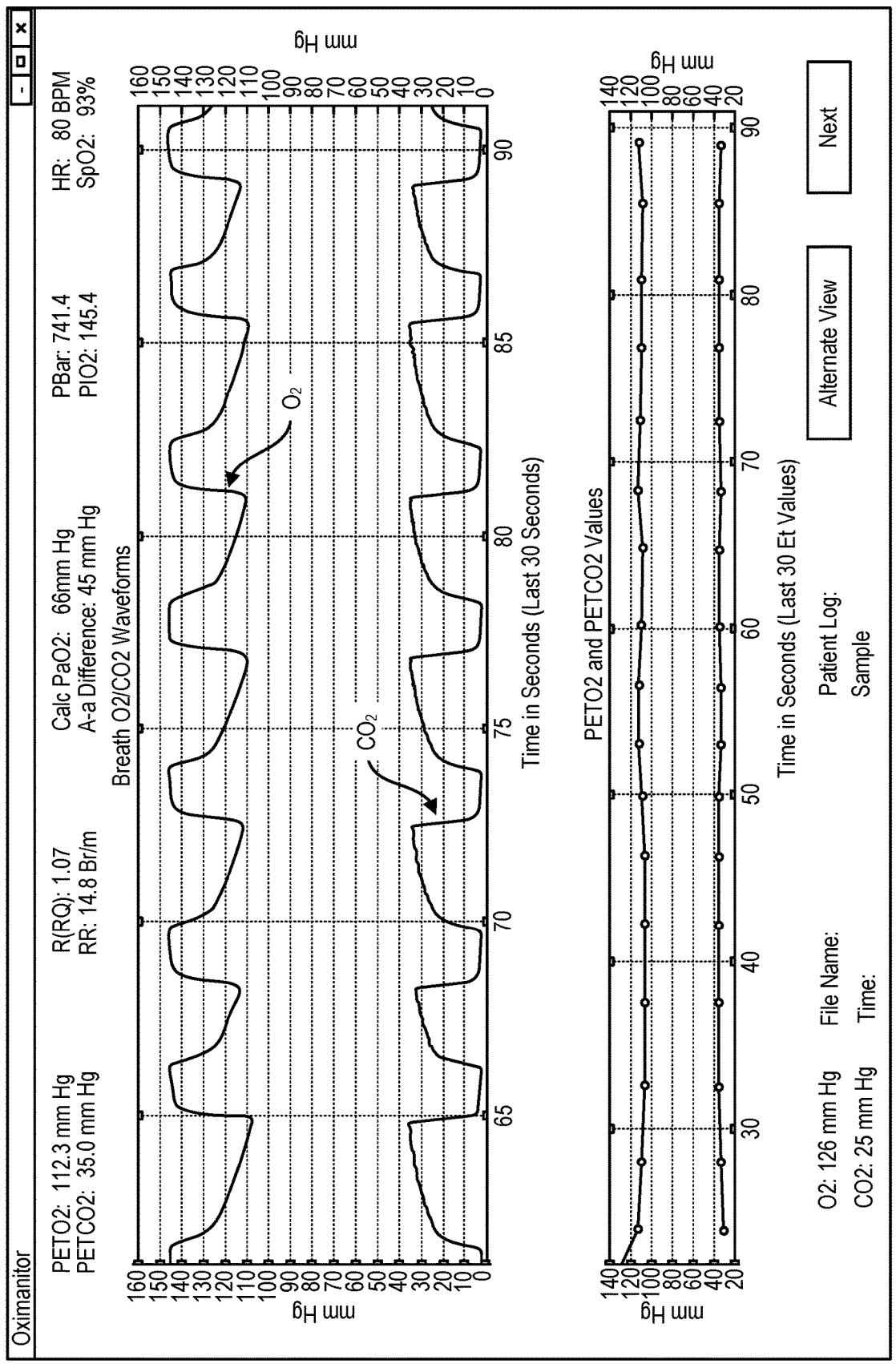
FIG. 5B is a diagram illustrating an exemplary output display including graphs showing breath by breath $O_2$ and $CO_2$ waveforms and values for various measured and calculated physiologic parameters, according to one implementation of the present disclosure.

FIG. 5B illustrates an example of a possible oximonitor output illustrating trends over time in detected alveolar oxygen and carbon dioxide levels. As shown, detected alveolar oxygen and alveolar carbon dioxide partial pressures may be displayed in separate curves with data points. Data points, curves or trendlines may be shown relative to baseline values for alveolar oxygen and alveolar carbon dioxide partial pressures established for a particular patient.

Figure 5C:
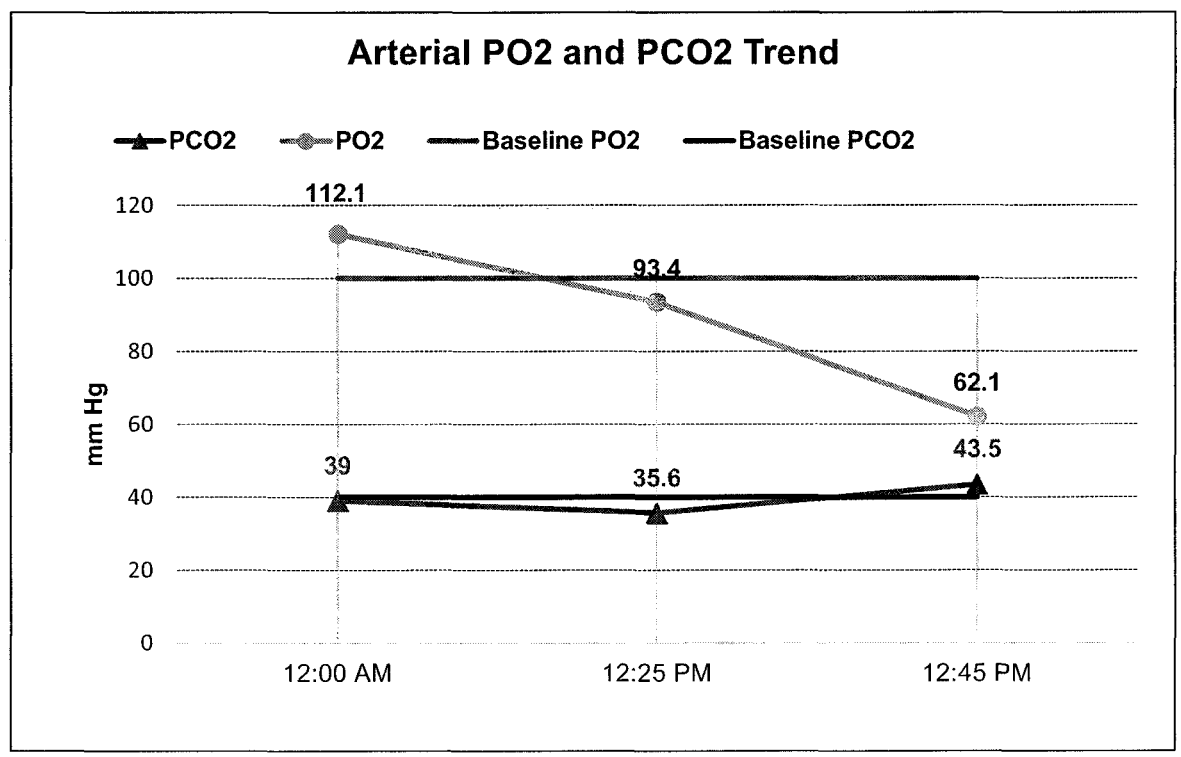
FIG. 5C is a diagram illustrating an exemplary graph showing trends in end-tidal arterial carbon dioxide partial pressure and end-tidal arterial oxygen partial pressure obtained from gas exchange tests performed on different times, according to one implementation of the present disclosure.

FIG. 5C illustrates an example of a possible oximonitor output illustrating trends in arterial oxygen and carbon dioxide partial pressures. As with the alveolar values shown in FIG. 5B, the arterial oxygen values may be shown as data points, curves, and/or trendlines, and may be shown relative to baseline values established for the patient. In the illustrated example, the decrease in arterial oxygen partial pressure over time may be indicative of a worsening gas exchange ability for the patient.

Figure 5D:
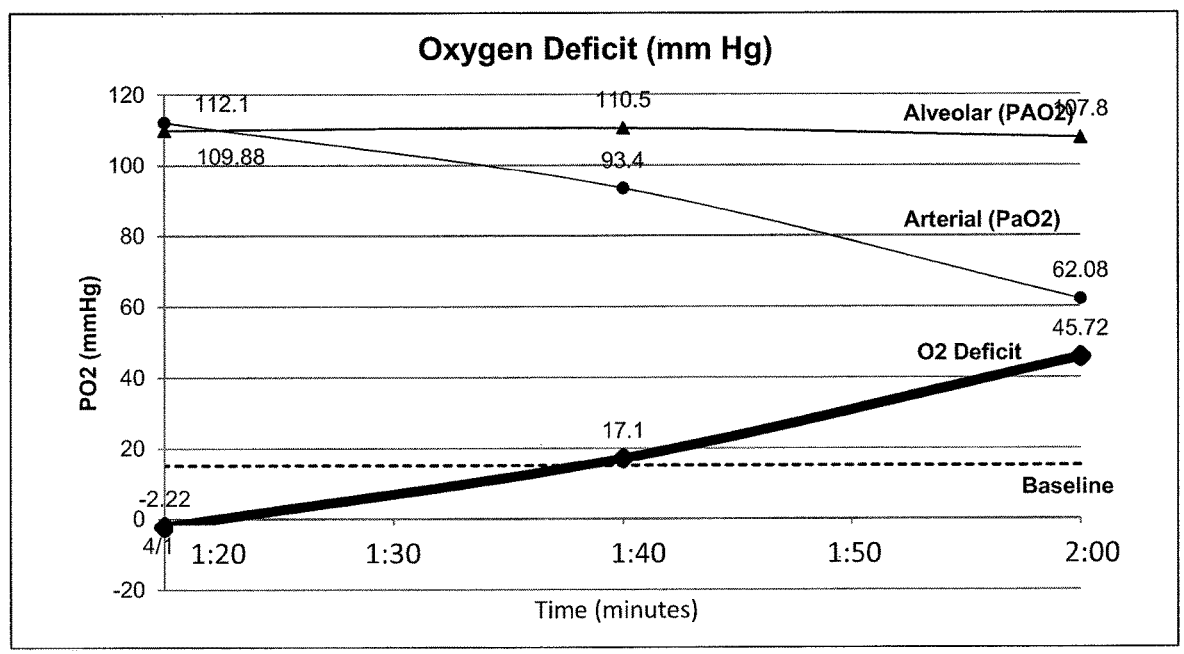
FIG. 5D is a diagram illustrating an exemplary graph of an oxygen deficit trend obtained from gas exchange test performed on various different times, according to one implementation of the present disclosure.

FIG. 5D illustrates an example of a possible oximonitor output illustrating an oxygen deficit trend along with alveolar and arterial oxygen trends. As above, trends may be shown relative to a baseline established for the patient. In some implementations, oximonitor system 100 may be configured to alert the patient and/or the patient's physician (e.g., by transmitting a message over a network) if oximonitor system 100 detects a value of oxygen deficit, alveolar oxygen, or arterial oxygen outside of a desired range relative to the baseline. For example, if oxygen deficit exceeds the baseline by at least a pre-determined amount and/or if arterial oxygen falls below the baseline by a pre-determined amount, the oximonitor system may transmit a message to a patient's physician alerting the physician of a deteriorating condition. The physician or other caregiver may set baseline values and/or deviation values at which an alert should be sent. In some implementations, changes triggered by acute events (such as a COPD patient catching Pneumonia) may result in a sharp rise in oxygen deficit. Frequent measurements of oxygen deficit may highlight the development of such problems before they progress dangerously.

Figure 6A:
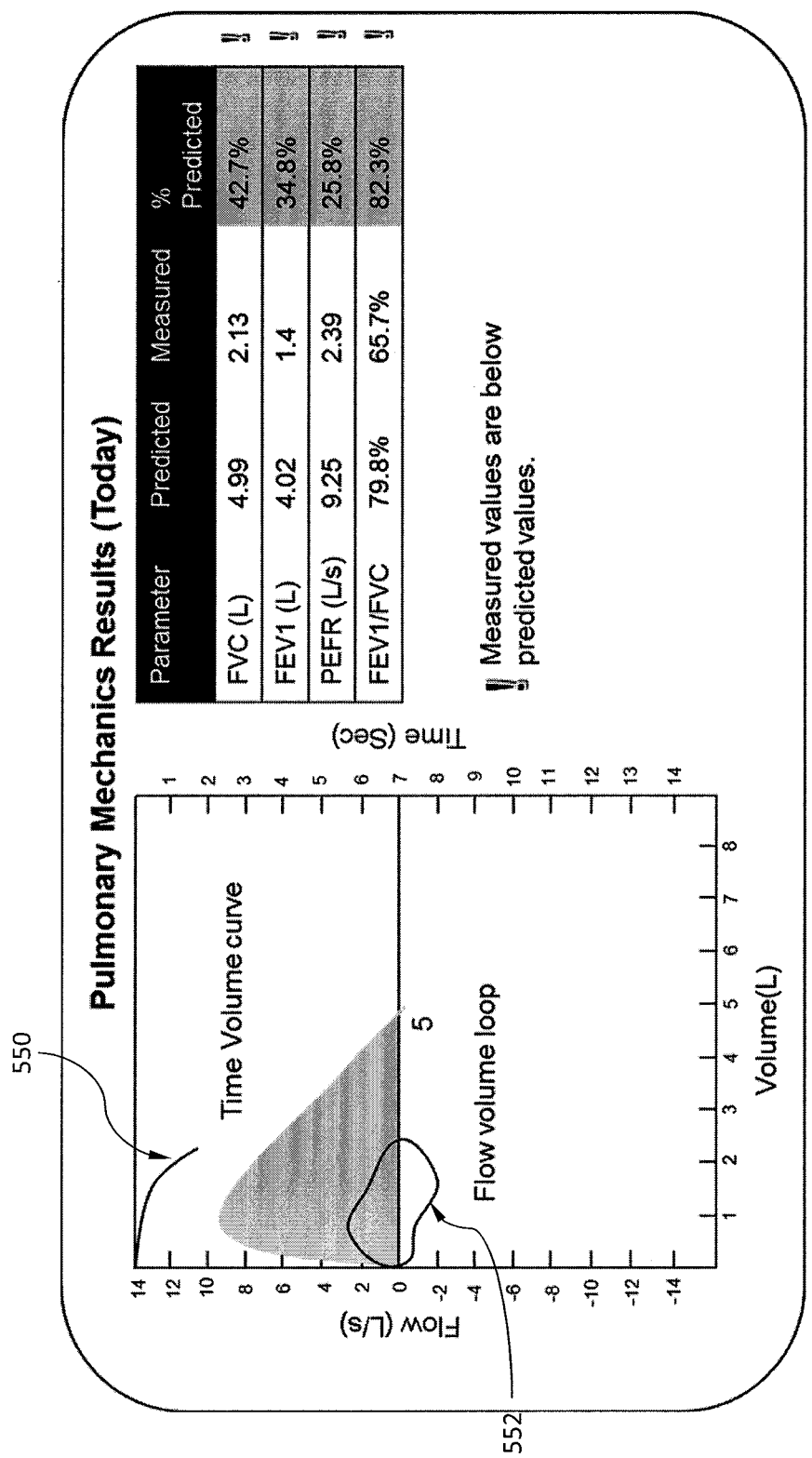
FIG. 6A is a diagram illustrating an exemplary graph of a Pulmonary Function Test performed on a single date, according to one implementation of the present disclosure.

FIG. 6A illustrates an example of a possible oximonitor output illustrating results from a pulmonary function test (PFT). A PFT can produce key measures that quantify the mechanical effectiveness of the lungs. Oximonitor system 100 may measure and display multiple parameters, including forced vital capacity (FVC, the total volume of air or breath expired during forced expiration), forced expiratory volume in one second ($FEV_1$, the volume of air or breath expired in one second during forced expiration), and peak expiratory flow rate (PEFR, the largest flow rate during forced expiration). In some implementations, the oximonitor device may also calculate and display a ratio of $FEV_1$ to FVC, which can indicate presence of some obstructive defects.

The left side of FIG. 6A illustrates a "flow-volume loop" 552 and a "volume time curve" 550 both displayed in the same graph. The right side of FIG. 6A includes a table with columns showing measured, calculated, predicted, and % predicted measures obtained from the PFT. The "predicted" values (which may be used in place of or in addition to "baseline" values determined by other methods) in both graphs and the table may be established based on a suitable standard such as population-based standards of the NHANES III spirometric reference standard recommended by the American Thoracic Society (or other suitable standards). In other implementations, oximonitor system 100 may be configured to allow physicians to set pulmonary mechanics baseline or predicted values to reflect a particular patient's situations and treatment routines. The % predicted values represent a percent variance of measured values relative to the established "predicted" or baseline values.

Figure 6B:
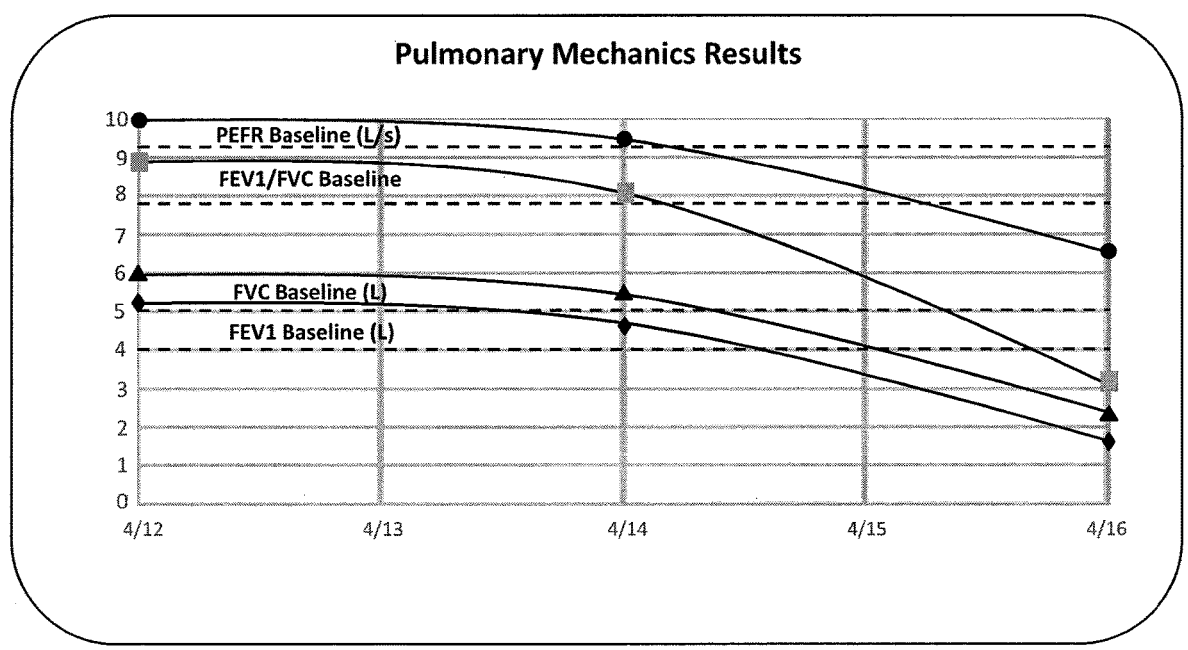
FIG. 6B is diagram illustrating an exemplary graph of a Pulmonary Function Test trend based on tests performed on different dates relative to a baseline, according to one implementation of the present disclosure.

FIG. 6B illustrates an example of a possible oximonitor output illustrating a pulmonary mechanics trend showing PFT results over a period of several days relative to baseline values shown as dotted lines. FIG. 6B displays four (4) key measures from the PFT and plots each measurement over time, showing trends over time.

Figure 7:
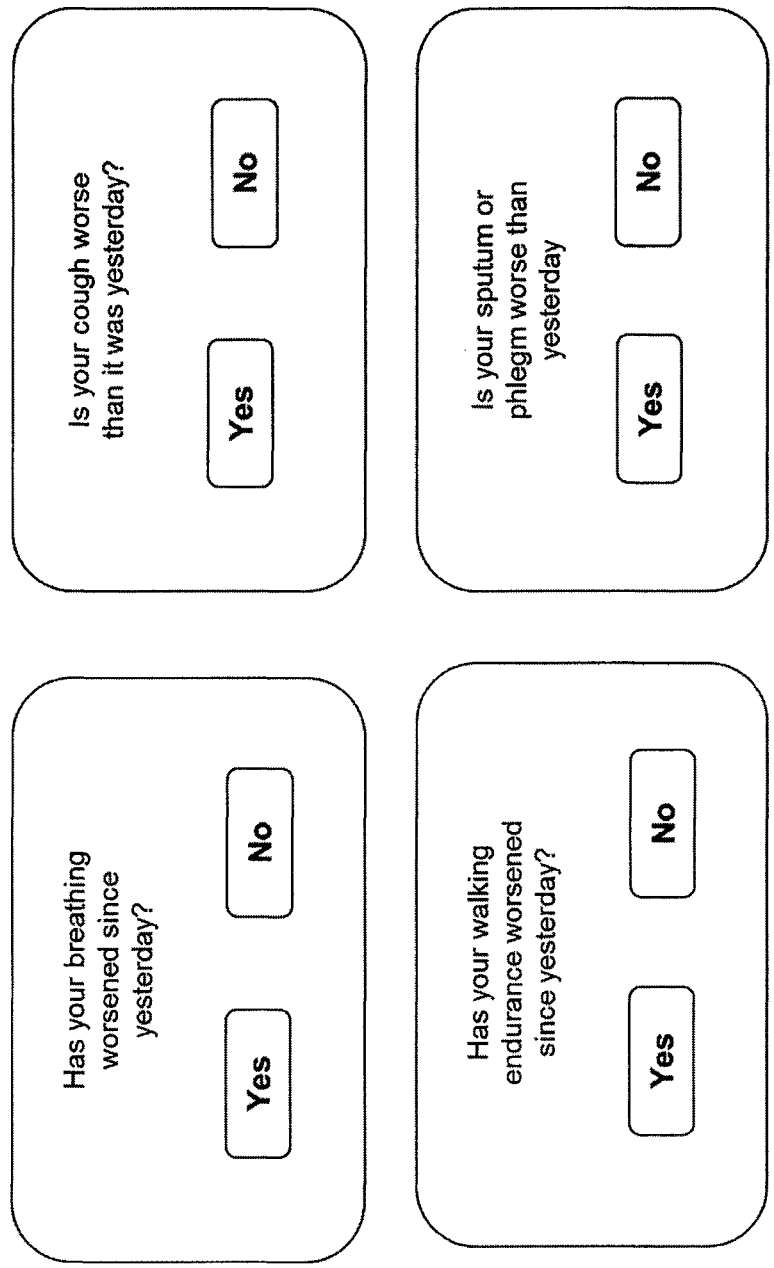
FIG. 7 is a diagram illustrating an exemplary patient symptom logger interface, according to one implementation of the present disclosure.

FIG. 7 illustrates an example user interface for an oximonitor symptom tracker, in which four (4) yes or no questions are asked. As shown, the questions include: "Has your breathing worsened since yesterday?", "Is your cough worse than it was yesterday?", "Has your walking endurance worsened since yesterday?" and "Is your sputum or phlegm worse than yesterday?" The questions may be provided on a touch-sensitive display screen, facilitating simple answering by a patient or a caregiver on behalf of a patient.

In various implementations, the data, metrics, and information collected during the tests performed by oximonitor system 100 may be used to diagnose and/or prescribe treatments for various breathing-related conditions.

As discussed above, existing tests for determining blood gas quantities are invasive (i.e., require skin puncture in order to withdraw blood) and time consuming. Even the currently-available ABG test equipment requires ½ hour or so to process a sample to obtain one measurement based on a single withdrawn blood sample. An ABG test also represents only a single snapshot of blood gas quantities at the time the blood is drawn. Continuous measurement of blood gas quantities is impossible with ABG testing methods.

Despite these limitations, ABG tests are recognized as the accepted standard in the industry for blood gas measurement. Some ABG testing systems also provide additional information, such as blood pH measurements, quantitative hemoglobin measurements, and others. In some implementations, one or more results from an ABG test may be used in combination with information from an oximonitor system. For example, in some implementations, an ABG test result may be used as a baseline against which more frequent or continuous measurements from an oximonitor system may be compared.

Many pulmonary or respiratory conditions tend to worsen quickly, but in ways that may not be immediately recognizable with conventional testing methods. For example, patients with chronic obstructive pulmonary disease (COPD) may suffer a sudden worsening of their respiratory condition as a result of environmental conditions or changes to other aspects of the patient's health. If such an "exacerbated" condition goes undiagnosed and untreated, permanent damage to the patient's respiratory system may result. Such "exacerbations" may be difficult to detect with conventional testing. For example, a drop in arterial oxygen saturation may be indicative of a worsening respiratory condition, but such a change may be too small to be reliably detected using a pulse oximeter to measure $SpO_2$. A fall of only 2% to 3% in $SpO_2$ may be indicative of a worsening condition, but such a small change may be more commonly attributed to normal variation in the accuracy of pulse oximetry measurement.

Therefore, clinicians and patients will greatly benefit from more instantaneous and continuous measurements of blood gas quantities that may allow for more accurate diagnosis of a worsening condition before the condition progresses to clinically dangerous levels. A change of only 2% to 3% in $SpO_2$ may correspond to a much larger (and therefore more detectable) change in $PaO_2$, $PaCO_2$, and/or oxygen deficit. An oximonitor system provides the ability for substantially instantaneous and continuous reporting of blood gas quantities, thereby providing substantial improvements to the technology of respiratory testing. Clinicians and patients may benefit from improved speed and accuracy in diagnosing a wide range of disorders relating to respiration, ventilation, and gas exchange.

Figure 8:
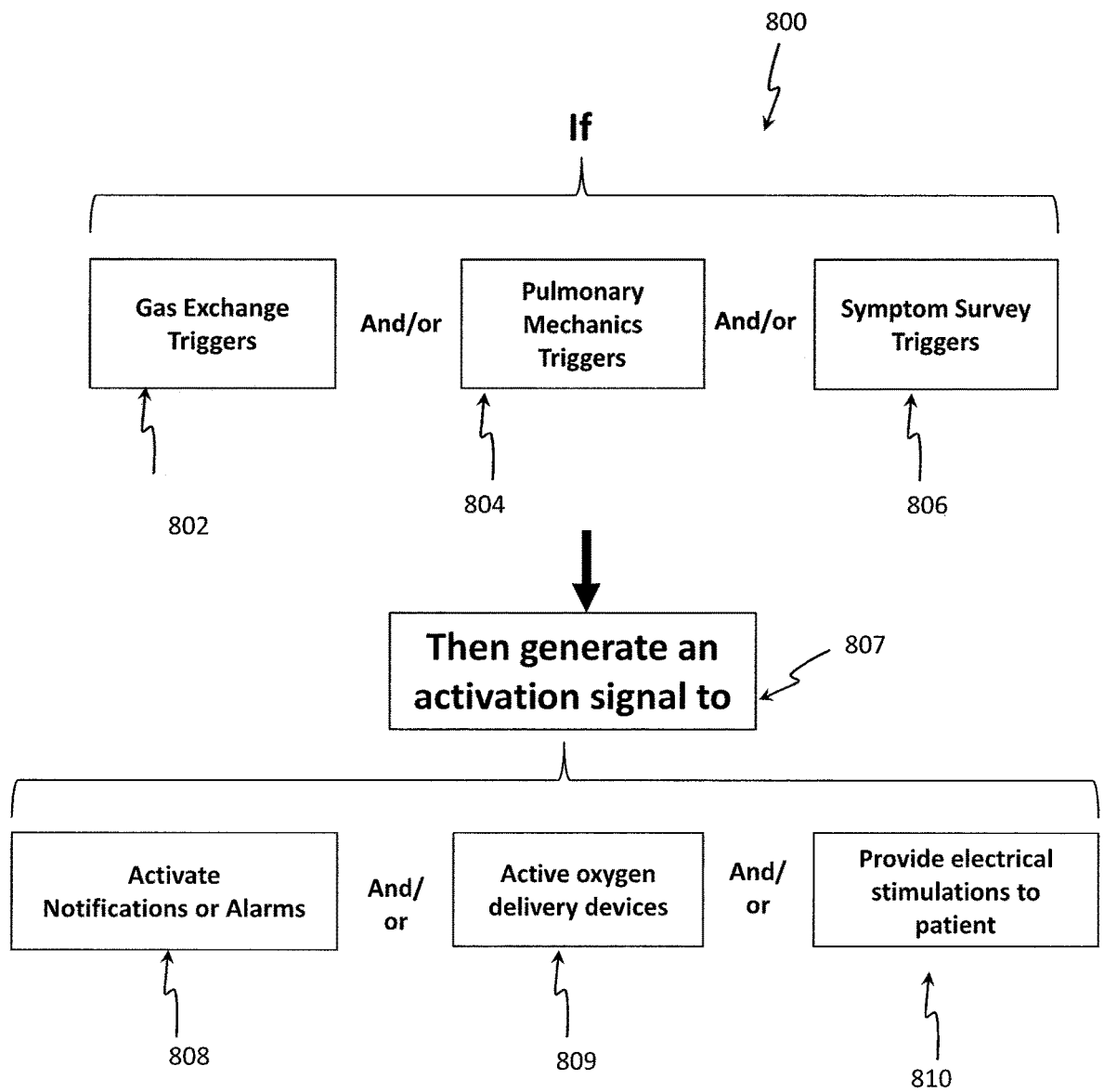
FIG. 8 is a process logic flow diagram illustrating exemplary conditions for activating an alarm, according to one implementation of the present disclosure.

Use of the oximonitor system 100 allows health care providers to make early decisions regarding changes of medication or other interventions, resulting in a great reduction in necessary hospital admissions for respiratory conditions. Patients and clinicians may also benefit from the ability to rapidly and non-invasively obtain an approximation of a patient's oxygen deficit in the form of an A-a gradient measurement. Continuous or frequently updated measures of oxygen deficit may provide valuable clinical information that is not practically available using ABG testing alone. Often, a patient's condition can change more quickly than can be practically detected using ABG testing. Rapid breath-based measurements of oxygen deficit can quickly alert clinicians to a patient's declining breathing condition, allowing the clinician to take corrective action before the patient's condition declines to dangerous levels. Additionally, because an oximonitor system may be configured to be portable, gas exchange test values may be obtained in settings where ABG testing is not practical or possible (e.g., in transit or remote locations with minimal access to a blood lab). FIG. 8 illustrates a process 800 for generating an activation signal that causes one or more of (1) triggering patient and/or caretaker notifications or alarms at 808, (2) activation of delivery of oxygen by an oxygen delivery device to the patient at 809, and providing electrical stimulations to the patient at 810, or (3) displaying, on a display device, a numerical or graphical output indicating one or more measured or calculated quantities. Notifications or alarms can be sound, visual display such as text or lights, and/or vibration of a device worn by the patient, or the care giver, such as wristband. In some implementations, alarm-triggering conditions may be established for each testing subsystem in oximonitor system 100. For example, oximonitor system 100 may contain gas exchange test alarm triggering conditions 802, pulmonary mechanics test alarm triggering conditions 804, and symptom survey alarm triggering conditions 806. A caregiver may treat the patient to reduce a health risk to the patient, such as risk of death, based on the determining of the arterial oxygen partial pressure ($P_aO_2$), the oxygen deficit ($P_AO_2$–$P_aO_2$) and the respiratory exchange ratio (RQ) of the patient.

In some implementations, an activation signal (e.g., at 808, 809, and/or 810) can be activated at 807 when one, two, or all three subsystem triggering conditions (e.g., at 802, 804, and/or 806) are met. In other implementations, an alarm may be triggered if alarm-triggering conditions are met for only one or only two subsystems.

In some implementations, if triggering condition(s) are met by one or more subsystems, an activation signal of electrical nature can be generated to activate a peripheral oxistimulator, such as that described in U.S. Pat. No. 8,417,351 ("the '351 patent"), which is incorporated herein by reference in its entirety. The '351 patent provides systems and methods for measuring a patient's blood oxygen content, and if blood oxygen content falls below a selected level, delivering peripheral nerve stimulation to the patient's wrist in the form of a milliamp current to arouse the patient. Such a system may be used to provide electrical stimulations to a patient at step 810 of the process of FIG. 8.

In other implementations, if triggering conditions are met by the system, an action signal of electrical nature can be generated to activate one or more oxygen delivery devices at 809, e.g. by operating a solenoid valve or by using a software interface to control oxygen via devices such as nasal prongs/cannulas, face masks, venturi masks, nebulizer, CPAP masks, IPPV/NIPPV masks, or transtracheal catheters.

In various implementations, one or more alarm triggering conditions 802, 804, and/or 806 may be defined so as to indicate possible presence of a particular medical condition. Some examples of medical conditions and example alarm triggering conditions 802, 804, and/or 806 are described below.

In various implementations, threshold values for alarm triggering conditions may be set based on a margin-of-safety in order to trigger an alarm or warning before a problematic condition is reached. In some implementations, multiple levels of alarm triggering conditions may be used. For example, a first alarm triggering condition (or threshold) may indicate a "mild" condition, a second alarm triggering condition (or threshold) may indicate a "moderate" condition, and a third alarm triggering condition (or threshold) may indicate a "severe" condition, each of which may be associated with a different activation signal to be generated upon the condition being met.

In some implementations, gas exchange test alarm triggering conditions 802 may be based on a single gas exchange measurement, an end-tidal measurement value for a single breathing cycle, a Boolean or mathematical combination of two or more gas exchange measurements, or one or more values calculated from two or more individual measurement values. As described above, some implementations of a gas exchange measurement system may be configured to directly measure $P_AO_2$, $PCO_2$, and $SpO_2$, and to use values from those measurements to calculate values including $P_aO_2$ and $O_2$ deficit.

In some implementations, a gas exchange test alarm condition may be met if a single measurement of $P_AO_2$ falls below a threshold. A single measurement of $P_AO_2$ may be an end-tidal value from a single breathing cycle or any other measurement during a breathing cycle. For example, a gas exchange test alarm condition may be met if a single end-tidal value of $P_AO_2$ from a single breathing cycle falls below about 90 or 80 mmHg.

In some implementations, a gas exchange test alarm condition may be met if multiple measurements (e.g., end tidal values from multiple breathing cycles) of $P_AO_2$ fall below a threshold within a specified period of time. For example, if two or more measurements of $P_AO_2$, obtained within about 30 seconds of one another fall below a threshold value, a gas exchange test alarm condition may be met. In another example, a patient's $P_AO_2$ may be measured over a trailing period of time (e.g., 10 seconds to two minutes or more) or a trailing number of breaths (e.g., two to 10 breaths or more), and an average $P_AO_2$ value may be calculated for the trailing period. A gas exchange test alarm condition may be met if the trailing period average $P_AO_2$ value falls below a threshold.

In some implementations, a gas exchange test alarm condition may be met if a single measurement of $PCO_2$ is greater than a threshold. In some cases, a relatively small increase in $PCO_2$ can be an ominous sign and will often alert a physician or other health care provider to take action. This may mean adjusting medications or possibly having the patient come to the physician's office or inpatient department for further investigation. A single measurement of $PCO_2$ may be an end-tidal value from a single breathing cycle or any other measurement during a breathing cycle. For example, a gas exchange test alarm condition may be met if a single end-tidal value of $PCO_2$ from a single breathing cycle is greater than about 45 mmHg.

Hypercapnia (also known as hypercarbia) is a condition of abnormally elevated $CO_2$ levels in the blood. Hypercapnia is generally defined as a blood gas carbon dioxide level ($P_aCO_2$) greater than 45 mmHg. Severe hypercapnia occurs at $P_aCO_2$ levels greater than 75 mmHg. Normal values of end-tidal $CO_2$ are about 35 to 37 mmHg. In normal lungs, end-tidal $CO_2$ may approximate arterial $CO_2$ concentration which tends to be only a few mmHg higher than the end-tidal values. Therefore, in some implementations, end-tidal $P_ACO_2$ measured using an oximonitor system may be treated as approximate values for $P_aCO_2$. In some implementations, $P_ACO_2$ values obtained with an oximonitor system may be adjusted by adding an adjustment quantity, e.g., 2, 3, 4, or 5 mmHg, to an end-tidal $P_ACO_2$ value to obtain an approximation of $P_aCO_2$. In some implementations, threshold values may be defined based on an approximate difference between end-tidal $P_ACO_2$ and $P_aCO_2$. For example, a threshold value of $P_ACO_2$ ($PCO_2$) may be about 40 mmHg or more. In other examples, a threshold value of $P_ACO_2$ ($PCO_2$) may be about 50 mmHg, 60 mmHg, 70 mmHg, or more.

In some implementations, a gas exchange test alarm condition may be met if multiple measurements (e.g., end tidal values from multiple breathing cycles) of $PCO_2$ are greater than a threshold within a specified period of time. For example, if two or more measurements of $PCO_2$ obtained within about 30 seconds of one another are greater than a threshold value, a gas exchange test alarm condition may be met. In another example, a patient's $PCO_2$ may be measured over a trailing period of time (e.g., 10 seconds to two minutes or more) or a trailing number of breaths (e.g., two to 10 breaths or more), and an average $PCO_2$ value may be calculated for the trailing period. A gas exchange test alarm condition may be met if the trailing period average $PCO_2$ value exceeds a threshold.

In some implementations, a gas exchange test alarm condition may be met if a single measurement of $P_aO_2$ falls below a threshold. As described above, in some implementations, an oximonitor system 100 may calculate one value of $P_aO_2$ per breathing cycle. In one example, a gas exchange test alarm condition may be met if a single end-tidal value of $P_aO_2$ from a single breathing cycle falls below about 80 mmHg. In other examples, $P_aO_2$ values less than about 60 mmHg, or less than about 40 mmHg may meet gas exchange test alarm conditions.

In some implementations, a gas exchange test alarm condition may be met if multiple $P_aO_2$ values fall below a threshold within a specified period of time. For example, if two or more $P_aO_2$ values obtained within about 30 seconds of one another fall below a threshold value, a gas exchange test alarm condition may be met. In another example, a patient's $P_aO_2$ may be measured over a trailing period of time (e.g., 10 seconds to two minutes or more) or a trailing number of breaths (e.g., two to 10 breaths or more), and an average $P_aO_2$ value may be calculated for the trailing period. A gas exchange test alarm condition may be met if the trailing period average $P_aO_2$ value falls below a threshold.

In some implementations, a gas exchange test alarm condition may be met if a single measurement of $O_2$ deficit is greater than a threshold. As described above, in some implementations, an oximonitor system may calculate one value of $O_2$ deficit per breathing cycle.

In some implementations, a gas exchange test alarm condition may be met if multiple measurements (e.g., based on multiple breathing cycles) of $O_2$ deficit are greater than a threshold within a specified period of time. For example, if two or more measurements of $O_2$ deficit obtained within about 30 seconds of one another are greater than a threshold value, a gas exchange test alarm condition may be met. In another example, a patient's $O_2$ deficit may be measured over a trailing period of time (e.g., 10 seconds to two minutes or more) or a trailing number of breaths (e.g., two to 10 breaths or more), and an average $O_2$ deficit value may be calculated for the trailing period. A gas exchange test alarm condition may be met if the trailing period average $O_2$ deficit value exceeds a threshold. In some examples, a gas exchange test alarm condition may be met if an $O_2$ deficit value from one or more breathing cycles is greater than about 9 (for young patients) to about 35 (for older patients) as indicated through an age adjustment calculation explained below.

A generally accepted rule-of-thumb is that a "normal" A-a gradient may be approximated by taking a patient's age divided by four and adding 4. Using such a calculated (or estimated) "normal" value as a baseline $O_2$ deficit, a gas exchange test alarm triggering conditions 802 may include an oxygen deficit exceeding a baseline value by a threshold amount. For example, in some implementations, a gas exchange test alarm condition may be met if the oxygen deficit exceeds an established baseline by between about 90% to about 150% (as a percent change from the baseline $O_2$ deficit). In some implementations, a gas exchange test alarm condition may be met if the oxygen deficit exceeds an established baseline by between about 110% and about 130%, and in one particular implementation about 125%. In some implementations, an oximonitor system 100 may be configured to take a patient's age as an input, and to calculate an estimated baseline $O_2$ deficit based on the entered age.

In some implementations, a gas exchange test alarm condition may be met if a rate-of-change of a gas exchange quantity (e.g., $P_AO_2$, $PCO_2$, $SpO_2$, $P_aO_2$, or $O_2$ deficit)

relative to time exceeds or falls below a threshold. For some gas exchange quantities, an alarm condition may be met if the rate of change is positive, while for others a negative rate of change may meet an alarm condition. In still other cases, any change (positive or negative) greater than a threshold may meet an alarm condition.

In various implementations, a rate of change during a pre-defined period of time or a pre-defined number of breathing cycles may be monitored and/or calculated to determine whether an alarm condition is met. In some implementations, a total change over a pre-determined period of time or number of breathing cycles a may be calculated and/or monitored to determine whether an alarm condition is met.

In various implementations, a process for determining a rate of change of a measured gas exchange quantity relative to time may be begin by measuring and/or calculating the gas exchange quantity (e.g., $P_AO_2$, $PCO_2$, $SpO_2$, $P_aO_2$, or $O_2$ deficit) during a known number of breathing cycles (predetermined or measured) within a known period of time (predetermined or measured), and obtaining an end-tidal value of $P_AO_2$ for each breathing cycle. A rate of change may be calculated by calculating an average change over the time period or an aggregate change over the time period. In some implementations, a total area under the curve may be calculated by integrating the measured data over the measurement time period. A similar process may be used to determine a rate of change of a gas exchange quantity per breathing cycle.

Hypoxemia is defined as an abnormally low concentration of oxygen in the blood. While the causes of hypoxemia may vary (e.g., hypoventilation due to asthma or COPD, among other causes), the condition itself may be identified as an arterial oxygen concentration below a "normal" value. If untreated, low oxygen levels within the body will eventually impair organ function, respiratory acidosis can result (pH is abnormally lower than 7.4) which can lead to respiratory failure.

Based on various clinical studies, clinicians identify "mild" hypoxemia by a $P_aO_2$ value of between 60 and 79 mmHg. "Moderate" hypoxemia is indicated by a $P_aO_2$ value of less than 60 mmHg but more than 40 mmHg, while a $P_aO_2$ value below 40 mmHg is typically considered severe hypoxemia. In various implementations, these values or values within these ranges may be used as alarm conditions in an oximonitor system in order to indicate mild, moderate, or severe hypoxemia, respectively. In some implementations, hypoxemia may be identified by a combination of a $P_aO_2$ below a threshold and an $SpO_2$ value below a threshold. For example, a $P_aO_2$ below 60 mmHg and an $SpO_2$ below 90% may be indicative of hypoxemia.

Hyperventilation is defined as breathing at an abnormally rapid rate resulting in decreased carbon dioxide levels and increased oxygen levels that produce faintness, tingling of the fingers and toes, and if continued, alkalosis (elevated blood pH, >7.4) and loss of consciousness. Thus, in some implementations, an oximonitor system 100 may include gas exchange test alarm triggering conditions 802 selected to indicate hyperventilation. Such alarm conditions may be met by one or more measurements of $PCO_2$ below about 35 mmHg and one or more contemporaneous measurements of $P_aO_2$ above about 100 mmHg.

In some implementations, alarm triggering conditions for an oximonitor system 100 may be configured to track the progress of patients with common pulmonary disease such as Chronic Obstructive Pulmonary Disease (COPD) or asthma, and to trigger alarms, notifications, or actions if problems are detected. Large numbers of these patients live in their homes and it is often medically necessary to follow their condition over the course of months or years. If these patients develop what is known as an exacerbation, that is a worsening of their chronic condition to an acute form as a result of an upper respiratory infection or exposure to an air pollutant, the changes can be readily be recognized using an oximonitor system 100. As the disease progresses, the arterial oxygen saturation ($SpO_2$) will fall but often the change is too small to be recognizable. However, the ability to measure the oxygen deficit (as described above with reference to Equation 4) allows a patient and their caregivers to be aware of the progress of the disease much more rapidly. Typically, over a period of time when a patient's condition is worsening, a patient's arterial oxygen saturation may fall by only 2% or 3% but their oxygen deficit will tend to increase by a much larger margin (e.g., 10 mm Hg) which is a much more easily recognized change.

In some implementations, pulmonary mechanics test alarm triggering conditions 804 may include a determination that a threshold number of PFT test parameters (e.g., including PEFR, $FEV_1/FVC$, $FEV_1$, and FVC) fall to or below a threshold level from their respective baseline values. For example, in various implementations, an alarm triggering condition may be met if one, two, three, four, or more PFT parameters fall more than a threshold quantity below their respective baseline values. In various implementations, an alarm triggering condition may be met if a threshold number of PFT parameters falls below their respective threshold values by between about 60% and about 100%. In some implementations, an alarm triggering condition may be met if a threshold number of PFT parameters falls below their respective threshold values by between about 70% and about 90%, and in one particular implementation about 75%.

In some implementations, symptom survey alarm triggering conditions 806 may include detection of patient responses indicating worsening symptoms for at least a threshold number of the symptoms tracked for at least a threshold period of time. In some implementations, an alarm triggering condition may be met if one, two, three, four, or more tracked symptoms show a worsening trend for a period of time from about one day to about a week (or more, in some implementations). In some implementations, an alarm triggering condition may be met if one, two, three, four, or more tracked symptoms show a worsening trend for between about two days and about five days, and in one particular implementation about three days. In various other implementations, other alarm-triggering values may be used, or other parameters may be used.

In one implementation, the generated activations signal may trigger an alarm, which may include one or more of audible sounds, vibrations, visible messages on a display, lights, or any other suitable alarm type. In some implementations, alarm messages may be sent as alert notifications to physicians by sending a message over a communications network, such as an email system, a patient management system, an SMS messaging system, or any other messaging system. In some implementations, an alert message sent to a physician may include test result data for a relevant time period (e.g., days, or weeks, or months prior to the alarm being triggered). In other examples, an alert message may contain a hyperlink or other pointer indicating a network resource from which the physician may retrieve test data relevant to the patient and/or to the alarm conditions.

In various implementations, data collected by an oximonitor system may be continuously or intermittently displayed on an output display device. Measurement data and/or calculated measurement data may be displayed numerically or graphically. In some implementations, some measurements may be displayed as continuously updated waveforms of measurement values vs time as illustrated, for example, in FIG. 9A.

Figure 9A:
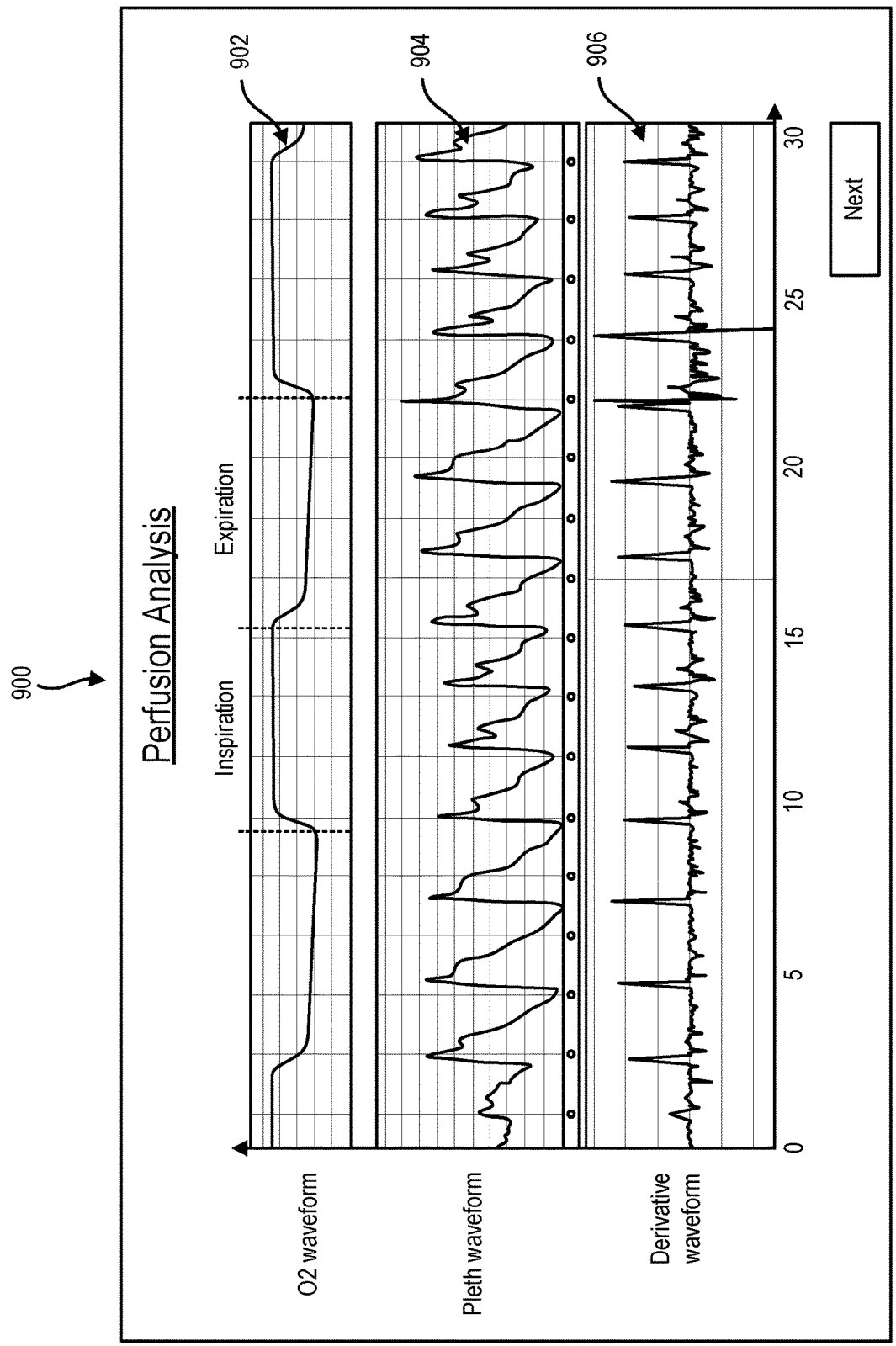
FIG. 9A is an illustration showing a graphical representation of waveforms illustrating breath by breath partial pressure of oxygen and corresponding blood flow volume measured by photoplethysmogram, according to one implementation of the present disclosure.

FIG. 9A illustrates one example display configuration showing a plurality of waveforms on aligned timeline (horizontal) axes. A first plot 902 shows an $O_2$ waveform over time, a second plot 904 shows a photoplethysmogram waveform over time, a third plot 906 shows a waveform of a second derivative of the photoplethysmogram over time. In one implementation waveforms are displayed over 30 seconds or 1 minute duration. In various implementations fewer or more breathing cycles may be displayed.

In some implementations, waveform plots may also display lines or waveforms indicating a baseline value (e.g., a trailing average from a longer time period than the displayed time period, a population-based expected value, or a value or waveform based on a clinician's judgment.

Figure 9B:
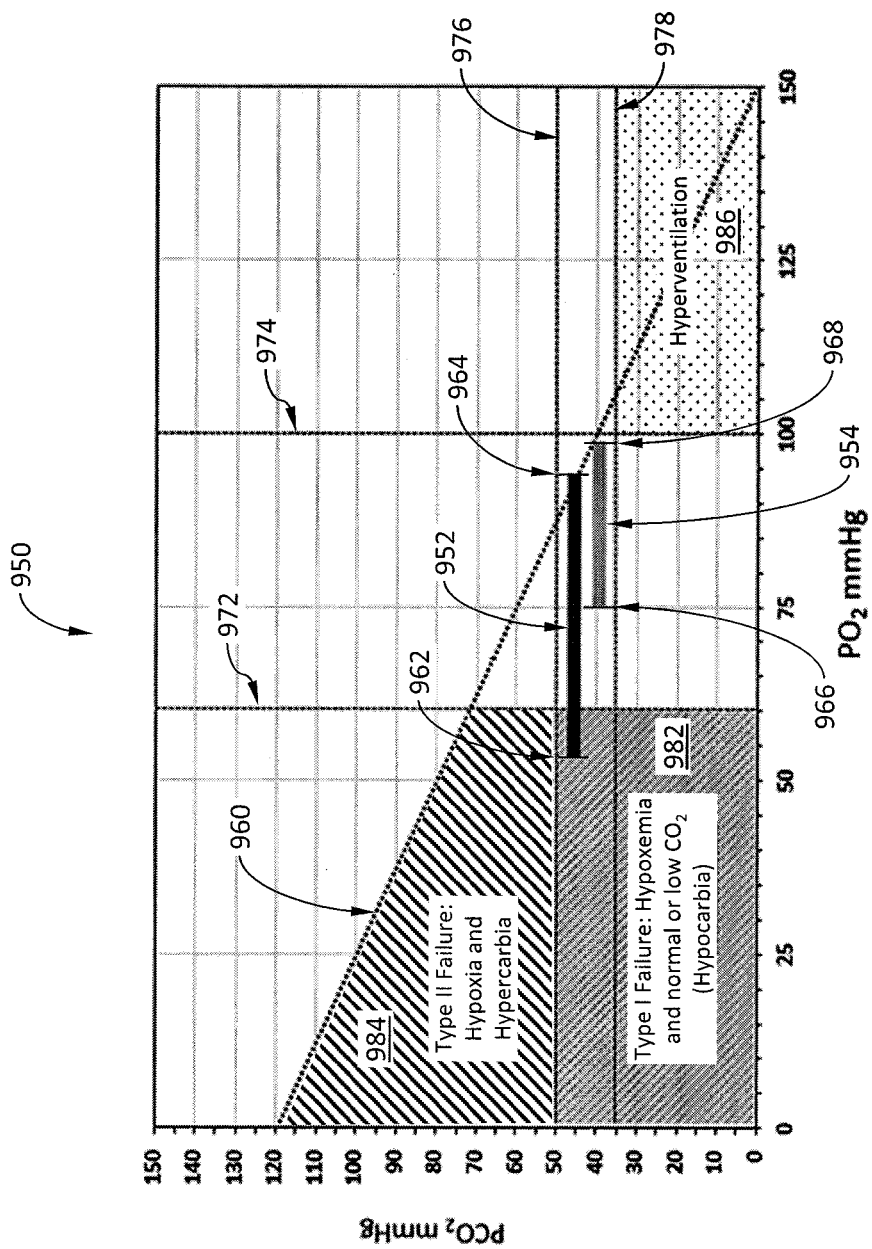
FIG. 9B is an illustration showing a different graphical representation of data and measurements obtained with an oximonitor system.

FIG. 9B illustrates another example graphical output that may be used to display data and measurements measured and calculated with an oximonitor system 100. FIG. 9B illustrates horizontal bars 952, 954 on a graph 950 of $PCO_2$ vs. $PO_2$. The location of the bars 952, 954 may be based on measurements obtained from an oximonitor system 100 (as explained further below). A diagonal line 960 may be displayed to represent a patient-specific alveolar gas line derived from the alveolar gas equation. In this example, the RQ value derived from the alveolar gas equation is given by Equation 5:

$$RQ=(PACO2*(1-FIO2))/(PIO2-PAO2-PACO2*FIO2) \quad \text{(Equation 5)}$$

Where $P_ACO_2$ is the measured partial pressure of alveolar $CO_2$ obtained by the oximonitor system, $P_CO_2$ is the partial pressure of oxygen in inhaled air given by Equation 6 below, $$P_1O_2=F_1O_2(P_{ATM}-pH_2O) \quad \text{(Equation 6)}$$

Where $F_1O_2$ is the fraction of inspired air that is oxygen, $P_{ATM}$ is atmospheric pressure, and $pH_2O$ is the saturated vapor pressure affecting the partial pressure of inspired oxygen. In many implementations, the value of $F_1O_2$ and $pH_2O$ may be assumed to be constant in most typical environments on Earth. Therefore, in many implementations, $P_1O2$ may vary only by atmospheric pressure which may be directly measured or assumed by an oximonitor system.

The respiratory quotient defines the slope of the alveolar gas line as the ratio of $CO_2$ eliminated to $O_2$ consumed by the patient and normal expected value of R=0.85. In some implementations, a respiratory quotient may be calculated based on measurements obtained by an oximonitor system. In other implementations, a respiratory quotient may be determined using an ABG test, and the respiratory quotient value may be manually or automatically entered into an oximonitor system.

The alveolar gas equation provided as Equation 1 above is a linear equation with a slope equal to the respiratory quotient, RQ. Given a value of RQ, the measured alveolar gas quantities $P_ACO_2$ and $P_AO_2$ should fall along the alveolar gas line 960. In various implementations, the alveolar gas line 960 may be displayed or not displayed on a graph 950. In some implementations, the system may display three direct patient gas measurements on one graph where patient specific data are plotted against oxygen partial pressure (PO2) on the X-axis, partial pressure of carbon dioxide (PCO2) on the Y-axis and the respiratory exchange ratio (RQ) of the patient as a slope on a single computer display. An increase or a decrease in the slope from standard RQ line may indicate the presence of on-going acid-base (pH) imbalance of blood and physiological compensatory mechanism is present. For example, the rise in the slope of the RQ line from the standard reference may suggest the presence of a metabolic acidosis, for which trending may provide signs of compensation to correct the imbalance.

In the graph illustrated in FIG. 9B, a horizontal bar, such as bars 952 and 954, may be used to illustrate four values: the longitudinal (horizontal) center line of the bar 952 or 954 may be located at a value of $PCO_2$ equal to a measured end-tidal value of $PCO_2$ (e.g., from a single breathing cycle or a normalized value based on multiple breathing cycles), the left-side edge 962 of bar 952 (or left side edge 966 of bar 954) may be located at a point equal to an arterial partial pressure of oxygen ($P_aO_2$) calculated using the Breath $P_aO_2$ Relation, the right-side edge 964 of bar 952 (or the right side edge 968 of bar 954) may be located at a point equal to the alveolar partial pressure of oxygen ($P_AO_2$) measured by the oximonitor system, and the length of the bar 952 or 954 may represent the oxygen deficit (i.e., the difference between $P_AO_2$ and $P_aO_2$).

In some implementations, a displayed graph 950 may include a first bar 952 representing "recently" measured values and a second bar 954 representing "historical" or baseline values. In various implementations, historical values illustrated by a second bar 954 may be values obtained during a past time period (e.g., hours, days, or weeks prior to a "current" measurement) or a trailing period as described herein. In other implementations, other definitions of historical or baseline values may be used. In various implementations, one or more numeric values may be displayed along with one or both bars 952 or 954 to indicate one or more values such as $P_AO_2$, $P_aO_2$, $O_2$ deficit, or others.

In various implementations, colors may also be used to indicate information associated with the bars 952, 954. For example, colors may be used to distinguish the "historical" bar 954 from the "current" bar 952. As another example, if the "current" bar 952 is longer than the "historical" bar 954 indicating an increase in oxygen deficit, then an excess portion of the "current" bar 952 (i.e., a portion that exceeds the length of the "historical" bar 954) or the entire "current" bar 952 may be displayed in a different color (e.g., red, yellow, etc.) to indicate a potentially dangerous condition.

In some implementations the graph 950 may display features illustrating various danger zones. For example, a first vertical line 972 may display a location of a low-end threshold level of $PO_2$, a second vertical line 974 may display a location of a high-end threshold level of $PO_2$, a first horizontal line 976 may display a location of a high-end threshold level of $PCO_2$, and a second horizontal line 978 may display a location of a low-end threshold level of $PCO_2$. The locations of the zone lines 972, 974, 976, 978 may be based on population "normal" baselines or other baselines, and may be pre-determined or adjustable by a clinician or any other operator of an oximonitor system.

A first danger zone 982 may illustrate a zone within which measurements may indicate a Type I respiratory failure characterized by hypoxemia (i.e., an $O_2$ level below the low-end $O_2$ threshold line 972) and normal or low levels of $CO_2$, where a "low" level of $CO_2$ is a level below the low-end $CO_2$ threshold line 978. A second danger zone 984 may illustrate a zone within which measurements may indicate a type II respiratory failure characterized by hypoxia as indicated by a level of $O_2$ below the low-end $O_2$ threshold line 972, in addition to hypercarbia as indicated by a level of $CO_2$ above the high-end threshold line 976. A third danger zone 986 may illustrate a zone within which measurements may indicate hyperventilation characterized by an oxygen level above the high-end $O_2$ threshold line 974 and a $CO_2$ level below a low-end $CO_2$ threshold line 978.

The various controllers, computers, analyzers, and similar devices described herein may comprise any suitable analog and/or digital signal processing components, such as field-programmable arrays (FPGAs), digital signal processors (DSPs), programmable logic controllers (PLCs), analog-to-digital converters, power management circuits or controllers, filters, amplifiers, timers, counters, or other devices as needed.

Figure 10:
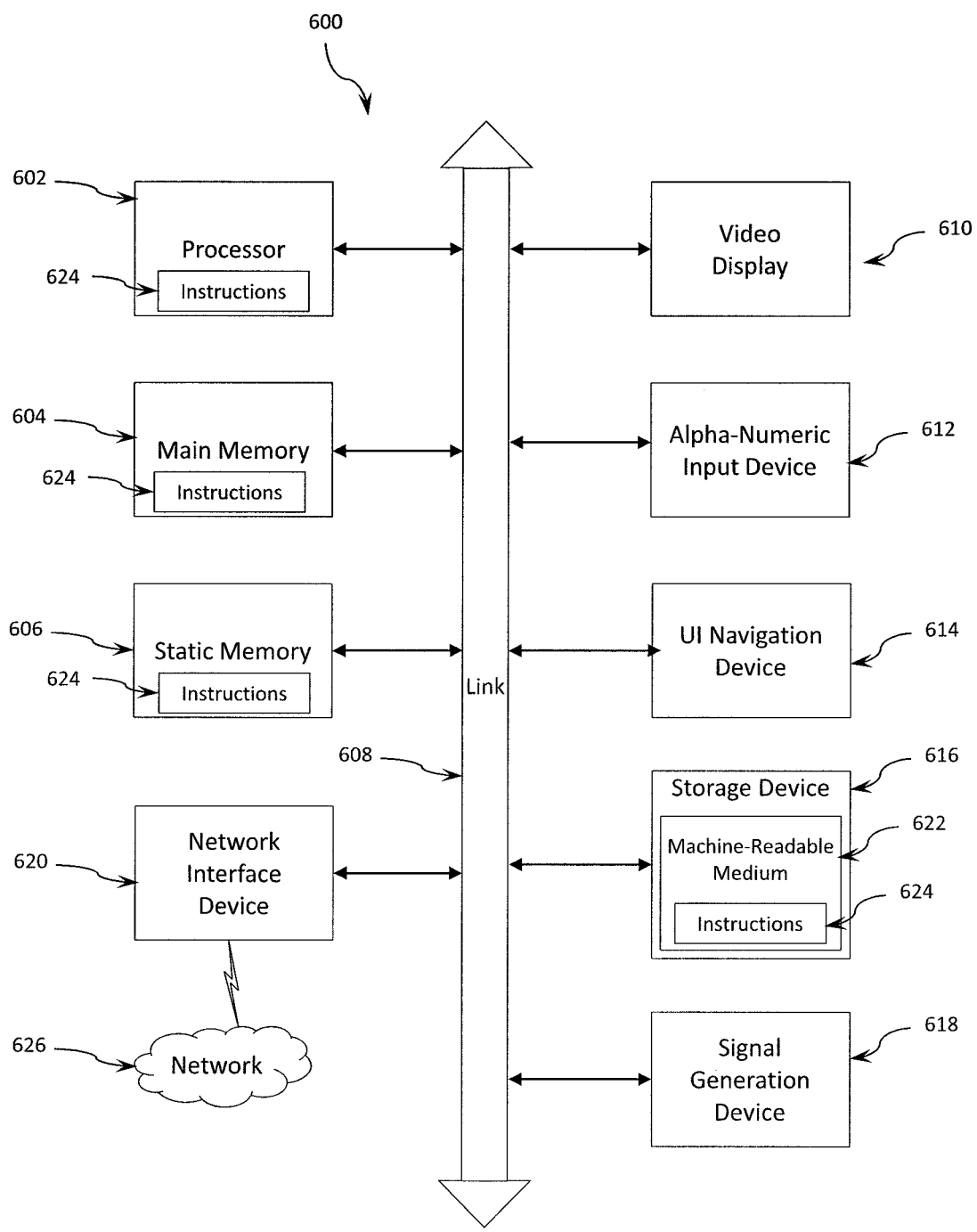
FIG. 10 is a schematic block diagram illustrating an exemplary computing device, according to one implementation of the present disclosure.

FIG. 10 is a block diagram illustrating an example computing machine 600 within which one or more sets or sequences of instructions may be executed to cause machine 600 to perform any one of the processes, methods, or calculations described herein, according to various example implementations. In some implementations, machine 600 such as that shown in FIG. 10 may operate as a standalone device or may be connected (e.g., networked) to other machines. In a networked deployment, machine 600 may operate in the capacity of a server or a client machine in server-client network environments, or a machine may act as a peer machine in peer-to-peer (or distributed) network environments.

Machine 600 may be a personal computer (PC), a laptop computer, a desktop computer, a server computer, a tablet PC, a hybrid tablet, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. For example, in some cases, a single physical machine may be configured to operate as multiple virtual machines by separately allocating resources of a physical machine to multiple separate processes.

Machine 600 includes at least one processor 602 (e.g., a central processing unit (CPU), and may include a graphics processing unit (GPU) or both, processor cores, compute nodes, one or more clocks, etc.), main memory 606 and static memory 606, which may communicate with each other via a link 608 (e.g., bus). Machine 600 may further include video display unit 610, alphanumeric input device 612 (e.g., a keyboard, touch screen, etc.), and user interface (UI) navigation device 614 (e.g., a mouse, touch pad, touch screen, etc.). In one implementation, video display unit 610, input device 612 and UI navigation device 614 may be incorporated into a touch screen display.

Machine 600 may additionally include one or more storage devices 616 (e.g., a drive unit), signal generation device 618 (e.g., a speaker), network interface device 620, and one or more sensors (not shown), such as a global positioning system (GPS) sensor, compass, accelerometer, or other sensor.

Storage device 616 (or devices) may include machine-readable medium 622 on which may be stored one or more sets of data structures and instructions 624 (e.g., software) embodying or utilized by any one or more of the processes, modules, methodologies or functions described herein. Instructions 624 may also reside, completely or at least partially, within main memory 604, static memory 606, and/or within processor 602 during execution thereof by the machine 600, with main memory 604, static memory 606, and processor 602 also constituting machine-readable media. In various implementations, instructions for separate modules or processes may be stored in storage regions on the one or more storage devices. Additionally, data stores, in the form of databases or other collections of data may also be stored in storage regions on the one or more storage devices. Storage regions may be physically contiguous or non-contiguous on the one or more storage devices, may be any size as needed, and may use any file management system, database management system, or data management system as desired.

While machine-readable medium 622 is illustrated in an example implementation to be a single medium, the term "machine-readable medium" may include a single medium or multiple media (e.g., a centralized or distributed database, and/or associated caches and servers) that store the one or more instructions 624. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions.

The term "machine-readable medium" shall accordingly be taken to include, but not be limited to, solid-state memories, and optical and magnetic media. Specific examples of machine-readable media include non-volatile memory, including, but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

Instructions 624 may further be transmitted or received over communications network 626 using a transmission medium via network interface device 620 utilizing any one of a number of well-known transfer protocols (e.g., HTTP, WAP, etc.). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or WiMAX networks). The term "transmission medium" shall be taken to include any tangible or intangible medium that is capable of storing, encoding, or carrying instructions for execution by the machine, and includes digital or analog communications signals or other medium to facilitate communication of such software.

Any of the devices (e.g., user devices), modules, data stores, servers, or other computing systems described in the various implementations herein may include some or all elements of machine 600 illustrated in FIG. 10 and described herein. For example, various components of an oximonitor system, such as computing device 202, controller 210, $O_2$ analyzer 224, $CO_2$ analyzer 222, the computer 202, or other components may be implemented with some or all elements of machine 600 described with reference to FIG. 10.

In one implementation, a medical device includes a breathing tube in fluid communication with an oxygen analyzer and a carbon dioxide analyzer, and in electronic communication with a computing device, a pulse oximeter in electronic communication with the computing device, and a pulmonary mechanics flow tube and a pulmonary mechanics controller in electronic communication with the computing device. The computing device may include software for collecting responses to patient symptom survey questions and for calculating a partial pressure of arterial blood oxygen based on contemporaneous measurements obtained with the carbon dioxide analyzer and the pulse oximeter.

In a further implementation, the computing device may include an alarm activation mechanism for notifying a patient and/or a physician responsible for the patient if at least three worsening conditions are met. In an additional implementation, an alarm is activated when a calculated oxygen deficit exceeds a pre-determined baseline value by at least a first threshold amount. In one implementation, the first threshold amount is between about 90% and about 150%. Also, an alarm may be activated when at least a second threshold number of pulmonary function test parameters fall to below respective pre-determined baseline values by at least a third threshold amount. In one implementation, the second threshold number of parameters is at least two, and the third threshold amount is between about 60% and about 100%, and an alarm is activated when at least a fourth threshold number of symptoms are indicated as worsening for a period of at least a fifth threshold time, and the fourth threshold number of symptoms is at least two, and the fifth threshold time is between about two days and about five days.

In yet another implementation, there is provided a method of measuring breathing-related metrics is provided that includes creating a time-series of pulse-oximetry measurements of a patient's peripheral arterial blood oxygen saturation during a first time period, and creating a time series of measurements of oxygen partial pressure and carbon dioxide partial pressure from exhaled air during steady-state breathing of the patient during the first time period.

In a further implementation, the method includes using the measured values to calculate additional metrics. In another implementation, the method includes calculating a partial pressure of arterial blood oxygen from a first selected set of the pulse-oximetry measurements and a second selected set of the carbon dioxide partial pressure measurements, and may also include calculating an oxygen deficit as a difference between a value representing the oxygen partial pressure measurements and the partial pressure of arterial blood oxygen.

In a further implementation, there is provided a method of non-invasively determining a partial pressure of oxygen in arterial blood. The method includes contemporaneously measuring a patient's peripheral arterial blood oxygen saturation with a pulse oximeter, measuring a partial pressure of carbon dioxide in the patient's exhaled breath, and using results of the blood oxygen saturation measurement and the carbon dioxide partial pressure measurement to calculate a partial pressure of arterial oxygen without drawing blood from the patient.

In another implementation, there is provided a method of non-invasively quantifying a patient's breathing efficiency. The method includes simultaneously measuring a patient's peripheral arterial blood oxygen saturation with a pulse oximeter, measuring a partial pressure of carbon dioxide in the patient's exhaled breath, measuring a partial pressure of alveolar oxygen in the patient's exhaled breath, using results of the blood oxygen saturation measurement, the carbon dioxide partial pressure measurement to calculate a partial pressure of arterial oxygen without drawing blood from the patient, and quantifying the patient's breathing efficiency based on a difference between the partial pressure of arterial oxygen and the partial pressure of alveolar oxygen.

In another implementation, there is provided a method of performing pulse-oximetry measurements of a patient's peripheral arterial blood oxygen saturation during a plurality of patient breathing cycles; aggregating or normalizing the peripheral arterial blood oxygen saturation measurements to obtain an average peripheral arterial blood oxygen saturation for the plurality of breathing cycles; performing oxygen partial pressure measurements and carbon dioxide partial pressure measurements from exhaled air during the same plurality of breathing cycles; obtaining an end-tidal value of oxygen partial pressure and an end-tidal value of carbon dioxide partial pressure for each breathing cycle; aggregating or normalizing the oxygen end-tidal values to obtain an average end-tidal oxygen partial pressure for the plurality of breathing cycles; and aggregating or normalizing the carbon dioxide end-tidal values to obtain an average end-tidal carbon dioxide partial pressure for the plurality of breathing cycles.

The method may further comprise calculating an average arterial partial pressure of oxygen for the plurality of breathing cycles using the average peripheral arterial blood oxygen saturation and the average end-tidal carbon dioxide partial pressure. The method may further comprise calculating an average oxygen deficit for the plurality of breathing cycles as a difference between the average arterial partial pressure of oxygen for the plurality of breathing cycles and the average alveolar partial pressure of oxygen for the plurality of breathing cycles.

The method may further comprise performing pulse-oximetry measurements of a patient's peripheral arterial blood oxygen saturation during an additional breathing cycle after the plurality of breathing cycles, and performing oxygen partial pressure measurements and carbon dioxide partial pressure measurements from exhaled air during the same additional breathing cycle; and updating the average peripheral arterial blood oxygen saturation, the average end-tidal carbon dioxide partial pressure, the average end-tidal oxygen partial pressure, the average arterial oxygen partial pressure, and the average oxygen deficit by removing data from a first of the plurality of breathing cycles and including data from the additional breathing cycle.

The method may further comprise continuously updating the average peripheral arterial blood oxygen saturation, the average end-tidal carbon dioxide partial pressure, the average end-tidal oxygen partial pressure, the average arterial oxygen partial pressure, and the average oxygen deficit in a first-in-first-out manner after each of an additional plurality of breathing cycles. The method may further comprise displaying a continuous waveform image of measured oxygen partial pressure and measured carbon dioxide partial pressure on a display device. The method may further comprise displaying continuous waveforms of arterial oxygen partial pressure or oxygen deficit, or both.

The method may further comprise displaying a graph having a carbon dioxide partial pressure axis and an oxygen partial pressure axis and including a first bar at a position relative to the carbon dioxide partial pressure axis indicative of the average end-tidal carbon dioxide partial pressure, a first end of the first bar positioned at a position indicative of the average arterial oxygen partial pressure, a second end of the first bar positioned at a position indicative of the average alveolar oxygen partial pressure, and a length of the bar indicative of the average oxygen deficit. The method may further comprise displaying a second bar at a position relative to the carbon dioxide partial pressure axis indicative of a historical end-tidal carbon dioxide partial pressure, a first end of the first bar positioned at a position indicative of a historical arterial oxygen partial pressure, a second end of the first bar positioned at a position indicative of a historical alveolar oxygen partial pressure, and a length of the bar indicative of a historical oxygen deficit, where the historical values are obtained from measurements performed prior to the plurality of breathing cycles.

The method may further comprise displaying an alveolar gas line on the graph. The method may further comprise displaying an indication of a region of the graph indicative of a Type I respiratory failure. The method may further comprise displaying an indication of a region of the graph indicative of a Type II respiratory failure. The method may further comprise displaying an indication of a region of the graph indicative of hyperventilation. The method may further comprise displaying lines indicating regions of the graph indicative of one or more of hypoxia, hypoxemia, hypercarbia, and hypocarbia.

In another implementation, there is provided a breathing mask with a resistance-free air conduit joining an interior of the mask to an exterior of the mask, and a transport tube joining the conduit to a gas analyzer circuit.

From the above description, it is manifest that various techniques can be used for implementing the concepts described in the present application without departing from the scope of those concepts. Moreover, while the concepts have been described with specific reference to certain implementations, a person of ordinary skill in the art would recognize that changes can be made in form and detail without departing from the scope of those concepts. As such, the described implementations are to be considered in all respects as illustrative and not restrictive. It should also be understood that the present application is not limited to the particular implementations described above, but many rearrangements, modifications, and substitutions are possible without departing from the scope of the present disclosure.

What is claimed is:

1. A method of using non-invasive procedures to indicate a patient's blood oxygen condition, the method comprising:
   receiving pulse-oximetry measurements ($SpO_2$) of a patient's peripheral arterial blood oxygen saturation;
   determining oxygen partial pressure measurements ($P_AO_2$) and carbon dioxide partial pressure measurements ($P_ACO_2$) from a steady-state breathing of the patient;
   determining at least one of (a) an arterial oxygen partial pressure ($P_aO_2$) and (b) an oxygen deficit ($P_AO_2-P_aO_2$) of the patient using at least one of the $SpO_2$ measurements, at least one of the $P_AO_2$ measurements, and at least one of the $P_ACO_2$ measurements; and
   continuously or frequently rendering on a display screen at least one of (a) an indication of the determined arterial oxygen partial pressure ($P_aO_2$) and (b) an indication of the patient's determined oxygen deficit.

2. The method of claim 1, wherein the oxygen partial pressure measurements ($P_AO_2$) and the carbon dioxide partial pressure measurements ($P_ACO_2$) are end-tidal values.

3. The method of claim 1 further comprising determining a respiratory quotient (RQ) of the patient using partial pressure of inspired oxygen measurements ($P_IO_2$), fraction of inspired oxygen measurements ($F_IO_2$), the oxygen partial pressure measurements ($P_AO_2$), and the carbon dioxide partial pressure measurements ($P_ACO_2$).

4. The method of claim 1, further comprising rendering an alarm signal based upon at least one of (1) the determined arterial oxygen partial pressure ($P_aO_2$) falling outside a pre-determined $P_aO_2$ threshold, (2) the determined oxygen deficit ($P_AO_2-P_aO_2$) falling outside a pre-determined oxygen deficit threshold, and (3) the determined partial pressure of carbon dioxide ($P_ACO_2$) falling outside a pre-determined $P_ACO_2$ threshold amount.

5. The method of claim 4, wherein the pre-determined oxygen deficit threshold is exceeding the patient baseline oxygen deficit by between 90% to 150%.

6. The method of claim 4, further comprising performing a plurality of pulmonary function tests and obtaining a plurality of pulmonary function test parameters during each pulmonary function test.

7. The method of claim 6, further comprising rendering an alternative alarm based on a determination that a threshold number of the plurality of pulmonary function test parameters has fallen below respective pre-determined pulmonary function test baseline values.

8. The method of claim 7, wherein the threshold number of the plurality of pulmonary function test parameters is at least two that have fallen below respective pre-determined pulmonary function test baseline values by between 60% and 100%.

9. The method of claim 1, further comprising obtaining responses to a plurality of patient symptom survey questions.

10. The method of claim 8, further comprising rendering a second alarm based on at least a threshold number of symptoms are indicated as worsening for a period of at least a threshold time.

11. The method of claim 4 further comprising:
   delivering oxygen to the patient, in response to the signal.

12. The method of claim 4 further comprising:
   providing an electrical stimulation to the patient, in response to the signal.

13. The method of claim 1 further comprising:
   treating the patient to reduce a health risk to the patient based on the determining of the at least one of the arterial oxygen partial pressure ($P_aO_2$), the oxygen deficit ($P_AO_2-P_aO_2$), and respiratory exchange ratio (RQ) of the patient.

14. A medical device configured to continuously or frequently render a low blood oxygen signal based upon non-invasive (a) information from a pulse-oximetry unit, and (b) breathing gas samples from a patient; comprising:
   a first port configured to receive pulse-oximetry measurements ($SpO_2$ values) from the pulse-oximetry unit;
   a second port configured to receive the breathing gas samples;
   a display screen; and
   a control unit configured to:
      determine $P_AO_2$ and $P_ACO_2$ values from the breathing gas samples;
      determine at least one of the patient's oxygen deficit and arterial oxygen partial pressure ($P_aO_2$) from all three of the $SpO_2$, $P_AO_2$, and $P_ACO_2$ values;
      display, on the display screen, a numerical or graphical output indicating the low blood oxygen signal based upon at least one of (i) the determined arterial oxygen partial pressure ($P_aO_2$) falling outside a pre-determined $P_aO_2$ threshold and (ii) the determined oxygen deficit ($P_AO_2-P_aO_2$) falling outside a pre-determined oxygen deficit threshold by at least a first threshold amount.

15. The medical device of claim 14, wherein the medical device is further configured to (a) deliver oxygen to the patient, in response to the low blood oxygen signal, or (b) provide an electrical stimulation to the patient, in response to the low blood oxygen signal.

16. The medical device of claim 14, wherein the control unit is further configured to determine a respiratory quotient (RQ) of the patient using partial pressure of inspired oxygen measurements ($P_IO_2$), fraction of inspired oxygen measurements ($F_iO_2$), the oxygen partial pressure measurements ($P_AO_2$), and the carbon dioxide partial pressure measurements ($P_ACO_2$), wherein the low blood oxygen signal includes an activation signal causing the alarm condition is determined based on at least one of the arterial oxygen partial pressure ($P_aO_2$), the oxygen deficit ($P_AO_2-P_aO_2$), partial pressure of carbon dioxide ($P_ACO_2$), arterial to alveolar tension ratio ($P_aO_2/P_AO_2$), arterial to fraction of inspired oxygen ratio ($P_aO_2/F_iO_2$) and respiratory exchange ratio (RQ) of the patient.

17. The medical device of claim 14, wherein the oxygen partial pressure measurements ($P_AO_2$) and the carbon dioxide partial pressure measurements ($P_ACO_2$) are end-tidal values.

18. The medical device of claim 14, wherein the control unit is further configured to render an alarm when any of the following values falls outside their corresponding baseline values, arterial to alveolar tension ratio ($P_aO_2/P_AO_2$), arterial to fraction of inspired oxygen ratio ($P_aO_2/F_iO_2$), and respiratory exchange ratio (RQ).

19. The medical device of claim 14, wherein the control unit is further configured to continuously or frequently display the $SpO_2$, $P_AO_2$ and $P_ACO_2$ values.

\* \* \* \* \*

UNITED STATES PATENT AND TRADEMARK OFFICE
CERTIFICATE OF CORRECTION

| | |
|---|---|
| PATENT NO. | : 11,154,215 B2 |
| APPLICATION NO. | : 15/814902 |
| DATED | : October 26, 2021 |
| INVENTOR(S) | : Steve Lee and John B. West |

It is certified that error appears in the above-identified patent and that said Letters Patent is hereby corrected as shown below:

In the Claims

At Column 40, Line 3 change, "threshold amount." to --threshold.--

At Column 40, Line 26 change, "a second alarm based on" to --a second alternative alarm based on--

At Column 40, Lines 60, 61 and 62 change, "falling outside a pre-determined oxygen deficit threshold by at least a first threshold amount." to --falling outside a pre-determined oxygen deficit threshold.--

Signed and Sealed this
First Day of November, 2022

Katherine Kelly Vidal
*Director of the United States Patent and Trademark Office*